(12) United States Patent
Koh

(10) Patent No.: US 7,094,207 B1
(45) Date of Patent: Aug. 22, 2006

(54) SYSTEM AND METHOD FOR DIAGNOSING AND TRACKING CONGESTIVE HEART FAILURE BASED ON THE PERIODICITY OF CHEYNE-STOKES RESPIRATION USING AN IMPLANTABLE MEDICAL DEVICE

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 153 days.

(21) Appl. No.: 10/792,305

(22) Filed: Mar. 2, 2004

(51) Int. Cl.
*A61B 5/0295* (2006.01)
*A61B 5/04* (2006.01)
*A61B 5/0402* (2006.01)

(52) U.S. Cl. .................. 600/529; 600/324; 600/518; 600/538

(58) Field of Classification Search ............. 600/529, 600/324, 518, 538
See application file for complete search history.

(56) References Cited

U.S. PATENT DOCUMENTS

| | | | |
|---|---|---|---|
| 5,056,519 A | 10/1991 | Vince | 128/419 G |
| 5,476,483 A | 12/1995 | Bornzin et al. | 607/17 |
| 5,817,135 A | 10/1998 | Cooper et al. | 607/17 |
| 5,911,218 A * | 6/1999 | DiMarco | 128/200.24 |
| 6,128,534 A | 10/2000 | Park et al. | 607/17 |
| 6,331,536 B1 * | 12/2001 | Radulovacki et al. | 514/214.02 |
| 6,415,183 B1 | 7/2002 | Scheiner et al. | 607/42 |
| 6,432,956 B1 | 8/2002 | Dement et al. | 514/252.1 |
| 6,454,719 B1 | 9/2002 | Greenhut | 600/484 |
| 6,459,929 B1 | 10/2002 | Hopper et al. | 600/513 |
| 6,512,952 B1 | 1/2003 | Stahmann et al. | 607/9 |
| 6,519,493 B1 | 2/2003 | Florio et al. | 607/6 |
| 6,525,073 B1 | 2/2003 | Mendel et al. | 514/337 |
| 6,586,478 B1 | 7/2003 | Ackman et al. | 514/738 |
| 6,589,188 B1 * | 7/2003 | Street et al. | 600/538 |
| 6,600,949 B1 * | 7/2003 | Turcott | 600/518 |
| 6,628,988 B1 | 9/2003 | Kramer et al. | 607/9 |
| 6,641,542 B1 * | 11/2003 | Cho et al. | 600/529 |
| 6,643,546 B1 | 11/2003 | Mathis et al. | 607/9 |
| 6,645,153 B1 | 11/2003 | Kroll et al. | 600/481 |

(Continued)

FOREIGN PATENT DOCUMENTS

EP 1151718 A2 4/2001

(Continued)

OTHER PUBLICATIONS

Thomas W. Millar, M. Sc., et al., "The Entrainment of Low Frequency Breathing Periodicity," *Chest*, 1990; vol. 98, pp. 1143-1148.

*Primary Examiner*—Robert E. Pezzuto
*Assistant Examiner*—Jason Rosenzweig

(57) ABSTRACT

Techniques are provided for distinguishing Cheyne-Stokes Respiration (CSR) caused by central sleep apnea (CSA) from CSR caused by congestive heart failure (CHF) and for evaluating the severity of CHF, if present, based up CSR. A time period associated with the CSR is determined based upon separate evaluation of apnea and hyperpnea periods during CSR and then the time period is compared against a time-varying discrimination threshold derived from integrated thoracic impedance signals. If the time period exceeds the threshold, the CSR of the patient is caused by CHF; otherwise, the CSR is caused by CSA. Thereafter, the course of therapy delivered to the patient is controlled based upon the type of CSR. In addition, if the CSR is caused by CHF, the time period associated with CSR is employed to determine the severity of CHF—with longer time periods being associated with more severe CHF.

20 Claims, 14 Drawing Sheets

U.S. PATENT DOCUMENTS

| | | |
|---|---|---|
| 6,830,548 B1 * | 12/2004 | Bonnet et al. .............. 600/529 |
| 6,839,581 B1 * | 1/2005 | El-Solh et al. .............. 600/324 |
| 2002/0002327 A1 | 1/2002 | Grant et al. ................ 600/324 |
| 2002/0193697 A1 | 12/2002 | Cho et al. ................... 600/529 |
| 2003/0153954 A1 | 8/2003 | Park et al. ................... 607/17 |

FOREIGN PATENT DOCUMENTS

| | | |
|---|---|---|
| WO | WO 01/76459 A2 | 10/2001 |
| WO | WO 01/76459 A3 | 10/2001 |
| WO | WO 02/087433 A1 | 11/2002 |

* cited by examiner

FIG. 10
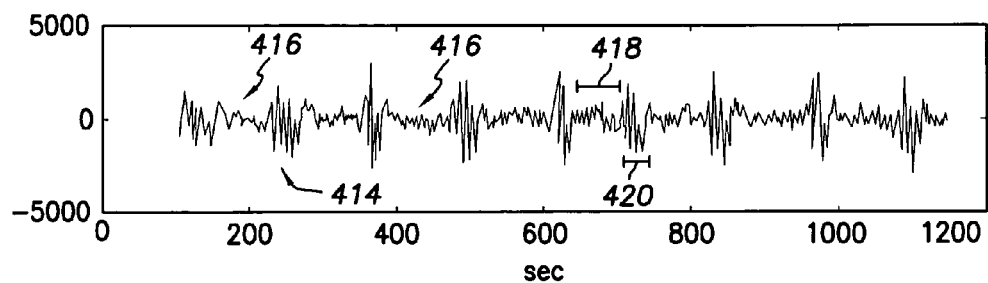
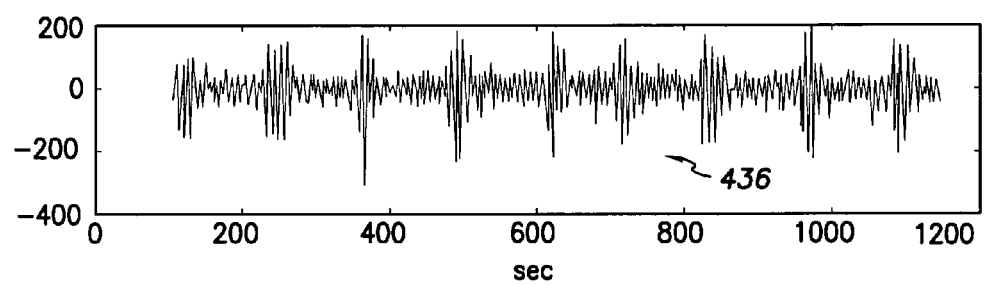
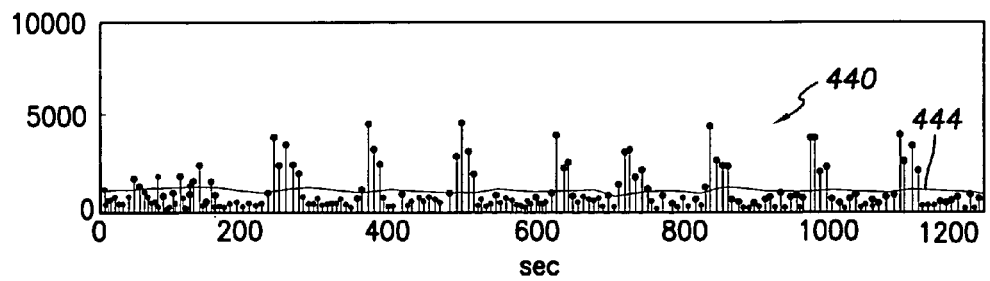

SYSTEM AND METHOD FOR DIAGNOSING AND TRACKING CONGESTIVE HEART FAILURE BASED ON THE PERIODICITY OF CHEYNE-STOKES RESPIRATION USING AN IMPLANTABLE MEDICAL DEVICE

CROSS-REFERENCE TO RELATED APPLICATIONS

This application is related to copending U.S. patent application Ser. No. 10/792,085, titled "System and Method for Diagnosing and Tracking Congestive Heart Failure Based on the Periodicity of Cheyne-Stokes Respiration Using an Implantable Medical Device", filed Mar. 2, 2004.

FIELD OF THE INVENTION

The invention generally relates to implantable medical devices, such as pacemakers or implantable cardioverter/defibrillators (ICDs) and, in particular, to techniques for detecting congestive heart failure (CHF) and for evaluating its severity within a patient in which a medical device is implanted.

BACKGROUND

CHF is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all CHF patients suffer debilitating symptoms immediately. Some may live actively for years. Yet, with few exceptions, the disease is relentlessly progressive. As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

CHF has been classified by the New York Heart Association (NYHA) into four classes of progressively worsening symptoms and diminished exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of CHF are present even at rest and where increased discomfort is experienced with any physical activity.

In view of the potential severity of CHF, it is highly desirable to detect its onset as early as possible. One technique for identifying CHF is to detect Cheyne-Stokes Respiration (CSR), which is an abnormal respiratory pattern often occurring in patients with CHF. CSR is characterized by alternating periods of apnea (i.e. a lack of breathing) and hyperpnea (i.e. fast, deep breathing.) Briefly, CSR arises principally due to a time lag between blood carbon dioxide ($CO_2$) levels sensed by the respiratory control nerve centers of the brain and the blood $CO_2$ levels. With CHF, poor cardiac function results in poor blood flow to the brain such that respiratory control nerve centers respond to blood $CO_2$ levels that are no longer properly representative of the overall blood $CO_2$ levels in the body. Hence, the respiratory control nerve centers trigger an increase in the depth and frequency of breathing in an attempt to compensate for perceived high blood $CO_2$ levels whereas the blood $CO_2$ levels have already dropped. By the time the respiratory control nerve centers detect the drop in blood $CO_2$ levels and slow respiration in response, the blood $CO_2$ levels have already increased. This cycle becomes increasingly unbalanced until respiration alternates between apnea and hyperpnea. The wildly fluctuating blood chemistry levels can exacerbate CHF and other medical conditions.

When CHF is still mild, CSR usually occurs, if at all, only while the patient is sleeping. Hence, the detection of CSR during sleep can be helpful in detecting the onset of CHF. However, CSR during sleep can also be caused by central sleep apnea (CSA), a neurogenic sleep disorder. When blood $CO_2$ levels exceed a certain threshold, the respiratory control nerve center of the brain generates a burst of nerve signals for triggering inspiration. The nerve signals are relayed via phrenic nerves to the diaphragm and via other nerves to chest wall muscles, which collectively contract to expand the lungs. With CSA, the nerve signals are not properly generated for periods of time while the patient is asleep or are of insufficient magnitude to trigger sufficient muscle contraction to achieve inhalation. In either case, the patient thereby fails to inhale until appropriate respiratory nerve signals are eventually generated—at which point fast, deep breathing often occurs (i.e. hyperpnea) to compensate for the increased blood $CO_2$ levels arising due to the episode of CSA. Often, the episodes of CSA are fairly periodic and so periods of apnea alternate with periods of hyperpnea. In other words, CSR occurs.

Therapies can differ significantly depending upon whether the underlying medical condition causing CSR is CHF or is instead CSA. With CHF, drug therapy is preferred, typically centered on medical treatment using angiotensin converting enzyme (ACE) inhibitors, diuretics or digitalis. Cardiac resynchronization therapy (CRT) may also be employed, if a bi-ventricular pacing device is implanted. Briefly, CRT seeks to normalize asynchronous cardiac electrical activation and resultant asynchronous contractions associated with CHF by delivering synchronized pacing stimulus to both ventricles, or to one ventricle upon detection of intrinsic activity in the other ventricle. The stimulus is synchronized so as to help to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing". In contrast, to address CSA, an external breathing apparatus, such as a device providing continuous positive airway pressure (CPAP) therapy or bi-level positive pressure therapy (Bi-PAP), is employed. Overdrive pacing may be employed if a pacing device is implanted. Implantable phrenic nerve stimulators may be used as well to maintain inspiration during periods of CSA.

Accordingly, it would be desirable to provide techniques for distinguishing between CHF-induced CSR and CSA-induced CSR, particularly so that appropriate therapies can be exploited, and it is to this end that certain aspects of the invention are directed. Herein, CSR induced by CSA is also referred to as "CSR-CSA"; CSR induced by CHF is also referred to as "CSR-CHF".

An article entitled "The Entrainment of Low Frequency Breathing Periodicity", by Millar et al., (CHEST Vol. 98, No. 5, November 1990, pp. 1143–1148) provides data indicating that differences arise in the periodicity of CSR depending up whether CSR-CSA or CSR-CHF. The data suggests that the time period for CSR is higher in CSR-CHF patients than in CSR-CSA patients (or that the frequency of CSR is lower). Although the article does not suggest its exploitation within implantable medical systems, the periodicity of CSR, if properly detected, could potentially be used to distinguish CSR-CSA from CSR-CHF using an implantable medical device and aspects of the invention are directed to that end. Challenges, moreover, remain in determining how best to detect and exploit CSR periodicity within an implantable system for distinguishing CSR-CSA from CSR-CHF. For example, arousal from sleep during CSR can affect the measured periodicity of CSR, thus adversely affecting the viability of any discrimination technique based on CSR periodicity. Accordingly, other aspects of the invention are directed to specific techniques for exploiting CSR periodicity for distinguishing CSR-CSA from CSR-CHF to provide reliable results for use in an implantable system.

Once it has been confirmed that CSR within a patient is induced by CHF, it is desirable to track the severity of CHF, particularly to facilitate selection of appropriate CHF therapies or to titrate such therapies. The article by Millar et al. also provides data indicating that the time period for CSR is correlated with circulation delay within patients (wherein circulation delay was defined as the average time delay for blood to travel from the lungs to a sensor in the carotid artery.) Since a general increase in circulation delay within a patient is likely to be indicative of progression of CHF, the time period for CSR would appear to correlate with the severity of CHF. Although the article does not suggest its exploitation within implantable medical systems, the magnitude of the periodicity of CSR, if properly detected, could potentially be used to track the severity of CHF using an implantable medical device with patients subject to CSR-CHF. Hence, still other aspects of the invention are directed to providing such capability within an implantable system. Again, however, challenges remain in determining how best to detect and exploit the magnitude of the CSR periodicity within an implantable system for tracking the severity of CHF within patients subject to CSR-CHF. As mentioned above, arousal from sleep or other movements occurring during CSR can affect the periodicity of CSR, thus adversely affecting the viability of any CHF tracking technique based on the magnitude of CSR periodicity. Accordingly, still other aspects of the invention are directed to specific techniques for exploiting the magnitude of CSR periodicity for tracking CHF within CSR-CHF patients so as provide reliable results for use in an implantable system.

It is worth noting that others have recognized that frequency and cycle length of CSR may be used to measure the progression of CHF. See, U.S. Patent Application US2002/019367 of Cho et al. However, the patent application of Cho et al. does not appear to provide any indication of how frequency and cycle length are related to progression of CHF. There is no indication, for example, of whether an increase in CSR cycle length indicates that CHF is progressing or whether it is a decrease in CSR cycle length that instead indicates that CHF is progressing. In addition, there does not appear to be any recognition that the CSR within a patient might be the result of CSA rather than CHF or that arousal from sleep or other factors might significantly affect the manner by which frequency and cycle length are evaluated. Accordingly, it does not appear that the patent application to Cho et al. provides a viable system for tracking progression of CHF based on the periodicity of CSR, to which the present invention is directed.

SUMMARY

In accordance with a first embodiment, techniques are provided for distinguishing CSR-CSA from CSR-CHF within a sleeping patient using an implanted medical device. Briefly, while the patient is asleep, a periodicity associated with CSR is detected, and CSR-CSA is distinguished from CSR-CHF based on an evaluation of the periodicity. Herein, CSR "periodicity" refers to either a time period of CSR or a frequency of CSR, which are reciprocal concepts.

In an exemplary embodiment, the time period for CSR is calculated by combining an average duration of periods of sleep apnea during CSR with an average duration of bursts of breathing during CSR. The time period is then compared with a CSR time period discrimination threshold. If the time period exceeds the threshold, CSR-CHF is thereby detected; otherwise CSR-CSA is detected. Alternatively, a CSR frequency is compared against a CSR frequency discrimination threshold. To prevent calculation of an erroneous value for the time period due to arousal from sleep, an accelerometer or other sensor is used to detect patient movement and, if arousal is detected, the time period is rejected and a new time period is calculated once the patient resumes sleep and another episode of CSR begins. The discrimination threshold is initially calculated based on thoracic impedance. More specifically, signals representative of thoracic impedance sensed using leads implanted within the heart are low-pass filtered. The derivative of the filtered impedance signal is calculated and then zero-crossing points are identified. The derivative of the filtered impedance signal is then integrated between each pair of consecutive zero-crossing points to generate a set of integral values, which effectively restore valley-top-peak amplitudes. A moving average of the integrated values is then periodically updated for use as the discrimination threshold.

Therapy is then delivered depending up whether the CSR is caused by CSA or instead by CHF. If CSR is caused by CSA, overdrive pacing may be employed in an attempt to prevent further episodes of CSA for occurring to thereby prevent further episodes of CSR from occurring. Alternately, if an implantable drug pump is provided, appropriate anti-apnea medications may be delivered to the patient. If overdrive pacing or drug therapy fails to prevent the onset of additional episodes of CSA, an implantable alarm or an external bedside alarm is preferably employed to generate a warning signal to the patient to awaken the patient so as to terminate the episode of apnea and thereby prevent the onset of CSR-CSA. Alternatively, if a phrenic nerve stimulator is provided, rhythmic stimulation may be applied to the phrenic nerves to stimulate the diaphragm so as to mimic respiration, thus overcoming apnea and preventing the onset of CSR.

If CSR is instead caused by CHF, then CRT is preferably employed to improve cardiac function. Additionally, or in the alternative, overdrive pacing or drug therapy may be provided. As with CSR-CSA, if additional episodes of CSR develop, warning alarms are preferably employed to awaken the patient during periods CSR to awaken the patient to break the cycle of CSR and help stabilize blood chemistry levels.

In accordance with a second embodiment, techniques are provided for evaluating the severity of CHF within a patient suffering from CSR-CHF, again using an implanted medical device. Briefly, a periodicity associated with CSR is detected. The severity of CHF within the patient is evaluated based on the periodicity, with a relatively long CSR time period being indicative of more severe CHF than a relatively short CSR time period (or with a relatively low CSR frequency being indicative of more severe CSR than a relatively high frequency.)

In an exemplary embodiment, the periodicity for CSR is compared against a set of values representative of various levels of CHF, then CHF therapy is controlled based on the degree of severity. For example, control parameters for CRT may be adjusted based on the severity of CHF. Additionally, or in the alternative, the aggressiveness of overdrive pacing may be controlled or drug dosages provided via an implantable drug pump may be titrated based on the severity of CHF. As with the techniques summarized above, if additional episodes of CSR nevertheless develop, warning alarms are preferably employed to alert the patient during periods CSR to break the cycle of CSR and thereby help stabilize blood chemistry levels. In addition, techniques are provided for assessing the severity of CSR by using a trend derived from CSR periodicity (either duration or occurrences).

Thus, various techniques are provided for use with implantable medical device for discriminating CSR-CSA from CSR-CHF within a patient and for evaluating the severity of CHF within the patient, if subject to CSR-CHF. Other objects, features and advantages of the invention will be apparent from the detailed description to follow.

BRIEF DESCRIPTION OF THE DRAWINGS

The above and further features, advantages and benefits of the present invention will be apparent upon consideration of the present description taken in conjunction with the accompanying drawings, in which:

FIG. 10 is a stylized diagram of an episode of CSR illustrating impedance (Z), impedance differential (dZ) and integrated dZ;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable CSR Responsive System

Figure 1:
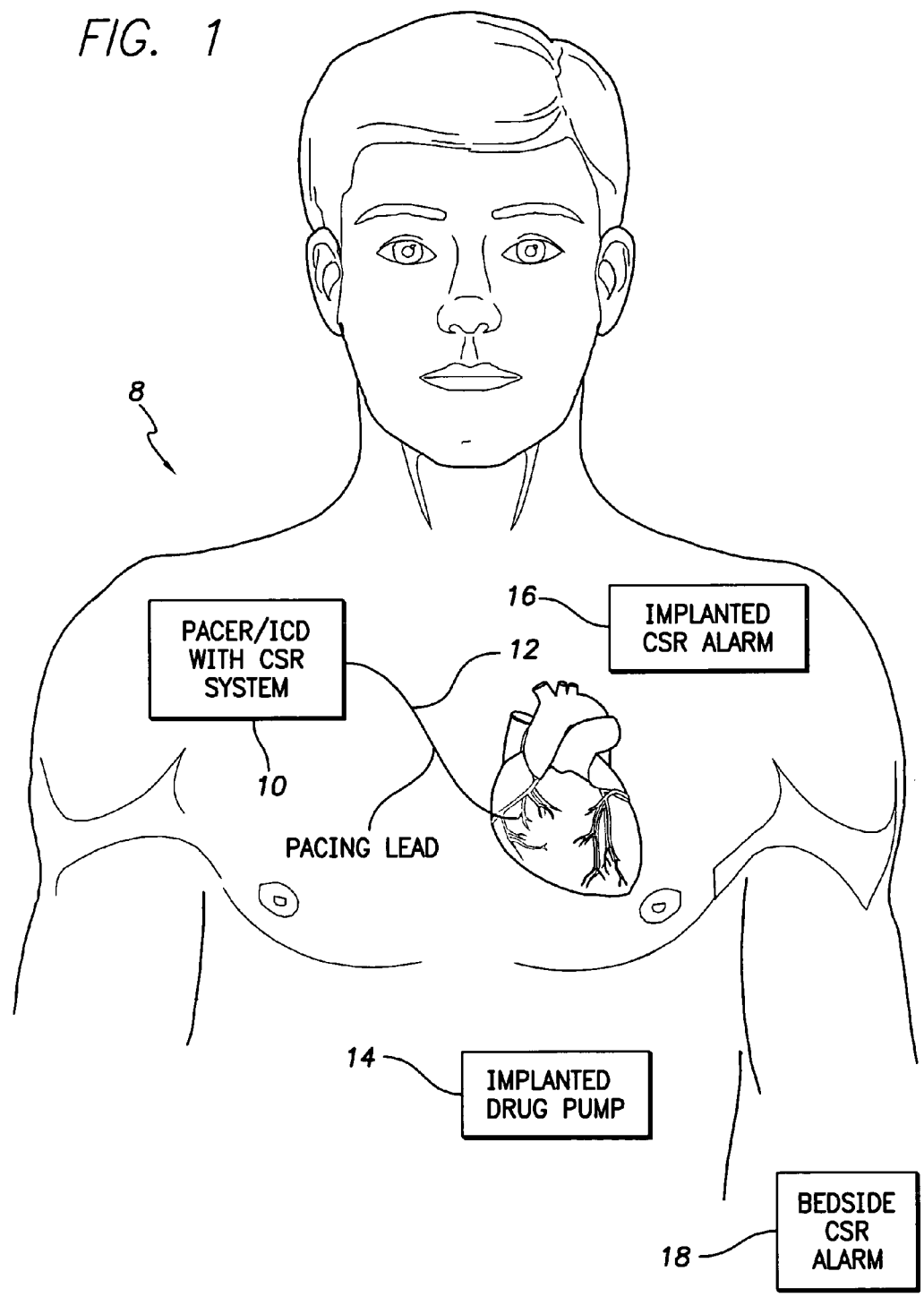
FIG. 1 illustrates pertinent components of an implantable CSR responsive medical system having a pacemaker or ICD capable of detecting episodes of CSR, distinguishing CSR-CSA from CSR-CHF based on CSR periodicity and delivering therapy in response thereto and also capable of tracking the severity of CHF also based on CSR periodicity.

FIG. 1 illustrates an implantable CSR responsive medical system 8 capable of detecting individual episodes of CSR, discriminating between CSR-CSA and CSR-CHF, evaluating the severity of CHF and delivering appropriate therapy. CSR responsive system 8 includes a pacer/ICD 10 or other cardiac stimulation device that incorporates internal components (shown individually in FIGS. 7 and 8) to that end. More specifically, pacer/ICD 10 receives signals from various cardiac pacing leads from which thoracic impedance is derived. In FIG. 1, only one exemplary lead 12 is shown.

Figure 6:
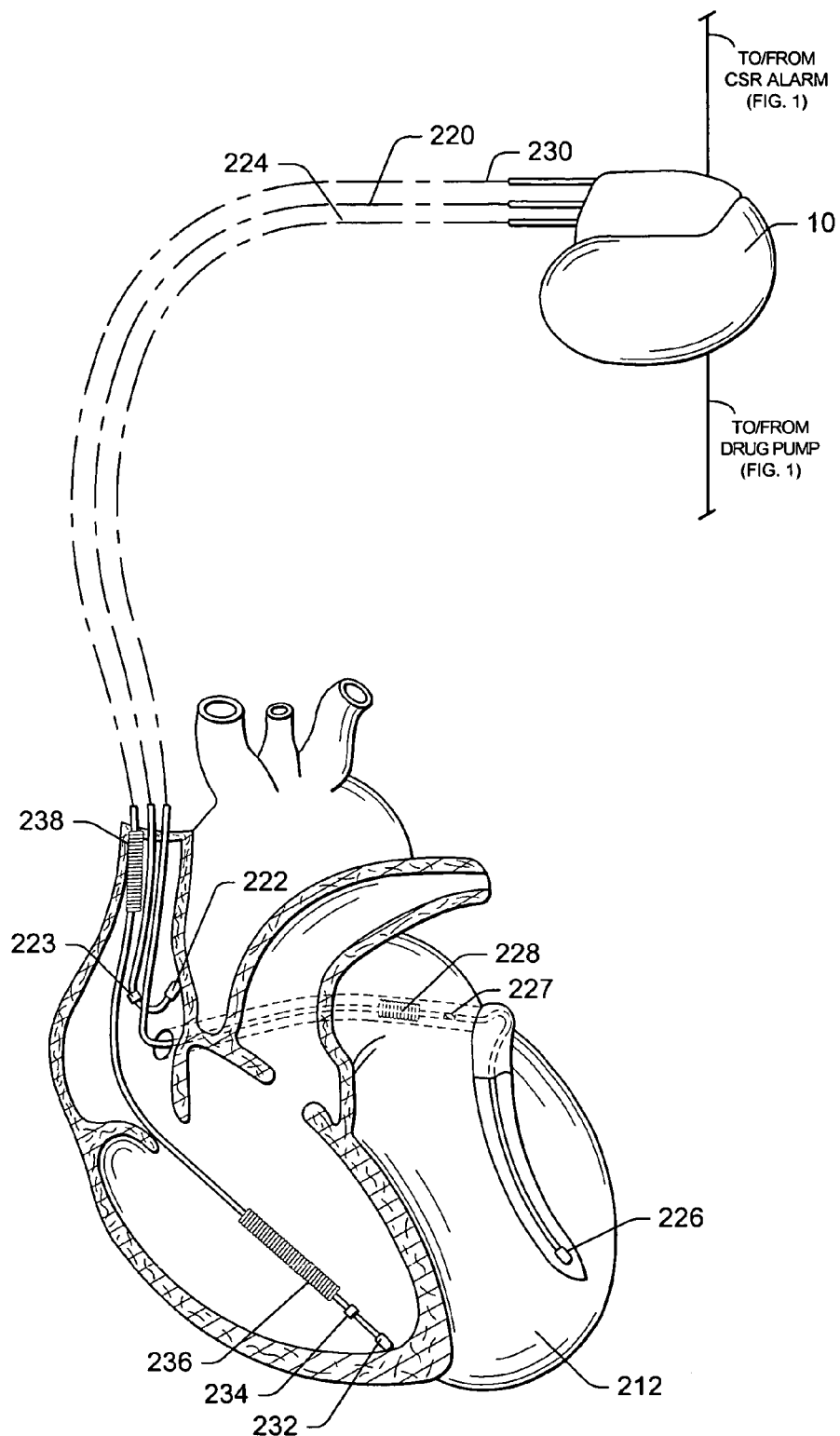
FIG. 6 is a simplified, partly cutaway view, illustrating the pacer/ICD of FIG. 1 along with at set of leads implanted into the heart of the patient.

Others pacing leads are shown in FIG. 6. Based on variations in thoracic impedance based by respiration, the pacer/ICD detects individual episodes of CSR, calculates the periodicity associated with the episodes of CSR and determines whether the individual episodes of CSR are caused by CSA or CHF based on the periodicity, so that appropriate therapy can be provided. For episodes of CSR caused by CHF, the pacer/ICD also evaluates the severity of CHF based on the periodicity. The pacer/ICD also tracks the progression of CHF based on any changes over time occurring in the CSR periodicity evaluated during CSR-CHF. Detailed descriptions of these techniques are set forth below.

If episodes of CSR are found to be caused by CHF, then appropriate therapy is automatically delivered by pacer/ICD. For example, CRT therapy may be applied using leads implanted in the ventricles so as to improve cardiac function in an effort to prevent additional episodes of CSR-CHF from occurring as well as to gain the other benefits of CRT. Additionally, or in the alternative, the implantable CSR responsive system may be equipped with a drug pump 14 capable of the delivering drug therapy in an attempt to address the underlying CHF. Discussions of possible medications for use in CHF patients are provided below. In addition, the pacer/ICD may be used to deliver DAO pacing for the purposes of preventing additional episodes of CSR-CHF from occurring. Control parameters for DAO and CRT therapy are adjusted based on the severity of the underlying CHF. Any drug dosages provided by an implantable drug pump may be titrated based on the severity of CHF. Hence, upon the detection of initial episodes of CSR-CHF, DAO and/or drug therapy is preferably delivered to the patient in an attempt to prevent the onset of additional episodes of CSR. If additional episodes nevertheless occur, then warning signals are generated using an either internal CSR alarm 16 or an external bedside alarm 18 to awaken the patient during CSR in an attempt to restore normal breathing and to thereby equalize blood chemistry levels. Internal alarm 16 may be a vibrating device or a "tickle" voltage device that, in either case, provides perceptible stimulation to the patient to awaken the patient. The bedside alarm may provide audible or visual alarm signals of sufficient magnitude to awaken the patient. In additional, once CSR-CHF has been detected, diagnostic in formation is stored for subsequent review by a physician or other medial professional. The physician may then prescribe any other appropriate therapies to address the CSR and the underlying CHF. The physician may also adjust the operation of the pacer/ICD to activate, deactivate or otherwise control any therapies that are automatically applied.

If the episodes of CSR are instead found to be caused by CSA, then CSA therapy is automatically delivered by pacer/ICD. If equipped with a drug pump, drug therapy may be delivered in an attempt to prevent additional episodes CSA to thereby prevent CSR-CSA. Discussions of possible medications for use with CSA are provided below. The pacer/ICD may also be deliver DAO pacing for the purposes of preventing additional episodes of CSA from occurring. As with CSR-CHF therapy, control parameters for DAO and CRT therapy applied to address CSR-CSA may be controlled based on the severity of the CSR. In addition, any drug dosages provided by an implantable drug pump to address CSA may be titrated based on the periodicity of the resulting CSR. Again, DAO and/or drug therapy is preferably delivered to the patient first in an attempt to prevent the onset of additional episodes of CSR. If additional episodes nevertheless occur, then warning signals are generated using either the internal CSR alarm or the external bedside alarm to awaken the patient during CSR-CSA to restore normal breathing and thereby equalize blood chemistry levels.

Although not shown, if the patient suffers from chronic CSA, implantable phrenic nerve stimulators may be implanted for use in responding to individual episodes of CSA. When an episode of CSA is detected, the pacer/ICD controls the phrenic nerve stimulators to rhythmically stimulate the diaphragm to cause the diaphragm to contract, thus mimicking breathing and thereby preventing CSR from arising as a result of CSA. The use of phrenic nerve stimulators are preferable within patients suffering from chronic CSA to allow individual episodes of CSA to be terminated before CSA causes CSR to occur so as to avoid the need to repeatedly awaken the patient. Techniques for detecting and treating sleep apnea are set forth in U.S. Patent Application: 2003/0153954 A1 of Park et al., entitled "Sleep Apnea Therapy Device Using Dynamic Overdrive Pacing".

Hence, FIG. 1 provides an overview of an implantable system for detecting individual episodes of CSR, discriminating between CSR-CSA and CSR-CHF, evaluating the severity of CHF if it is the cause of CSR, and delivering appropriate therapy. Internal signal transmission lines provided for interconnecting the various implanted components are not shown. Wireless signal transmission may alternatively be employed. In addition, it should be appreciated that systems provided in accordance with invention need not include all the components shown in FIG. 1. In many cases, for example, the system will include only the pacer/ICD and its leads with all therapy provide in the form of DAO or CRT. Drug pumps and CSR alarms are not necessarily implanted. Other implementations may employ phrenic nerve stimulators, but no internal or external alarms and no drug pumps. These are just a few exemplary embodiments. No attempt is made herein to describe all possible combinations of components that may be provided in accordance with the general principles of the invention. In addition, the particular locations of the implanted components shown in FIG. 1 are merely illustrative and may not correspond to actual implant location.

Overview of CSR Discrimination Technique

Figure 2:
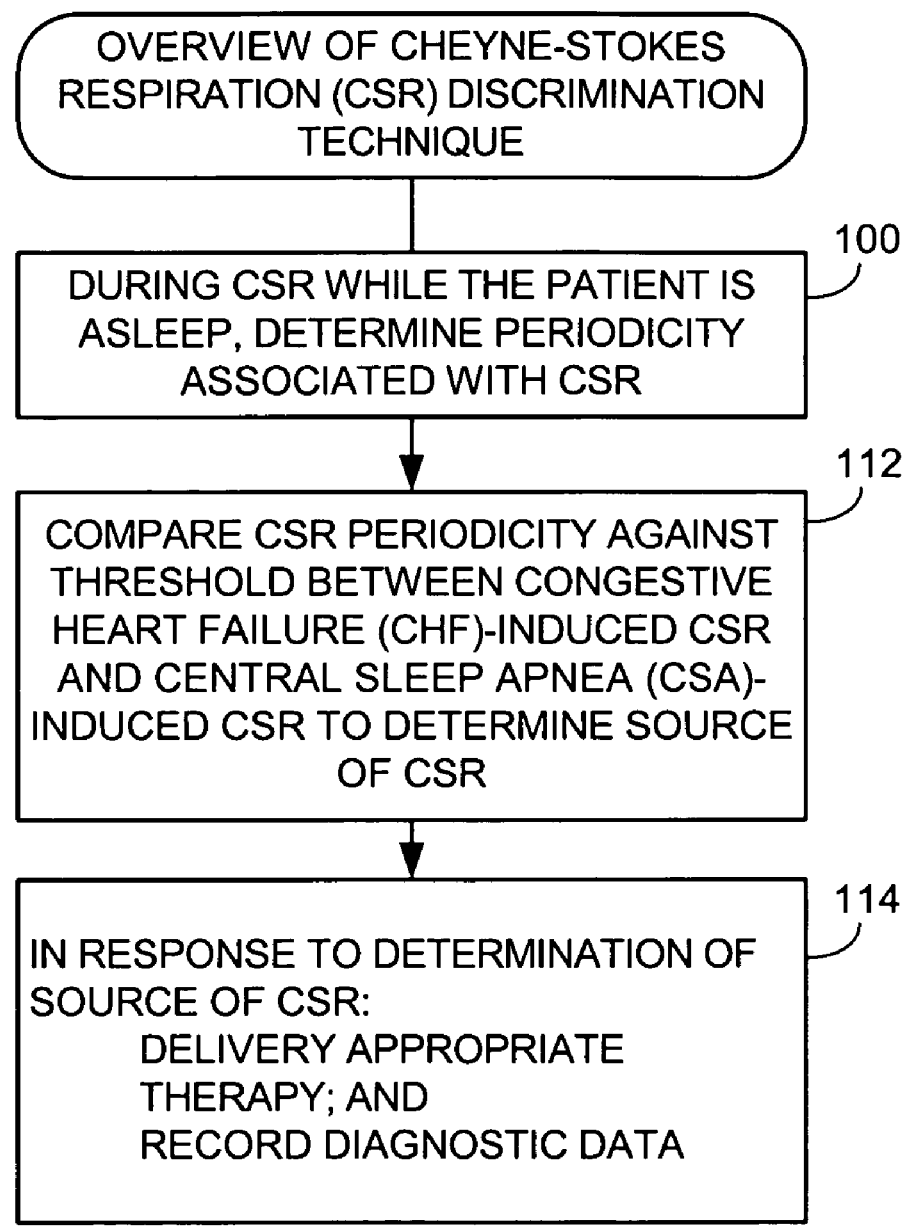
FIG. 2 is a flow diagram providing an overview of the method for discriminating between CSR-CHF and CSR-CSA as performed by the system of FIG. 1.

FIG. 2 provides an overview of the CSR discrimination technique of the invention. Initially, at step 100, the implantable pacer/ICD detects an episode of CSR while the patient is asleep then determines the periodicity associated with CSR. The technique is performed while the patient is asleep because CSR-CSA only occurs while a patient is asleep (since it arises due to a neurogenic disorder that only occurs during sleep.) In other words, if CSR occurs while a patient is awake, it should be due to CHF and so discrimination between CSR-CSA and CSR-CHF should not be required. The only time such discrimination is typically required is if CSR occurs while the patient is asleep. Note that CSR-CHF is far more common than CSR-CSA. Nevertheless, since the therapies to be applied may differ, it is desirable to discriminate between the two before delivering therapy.

Figure 3:
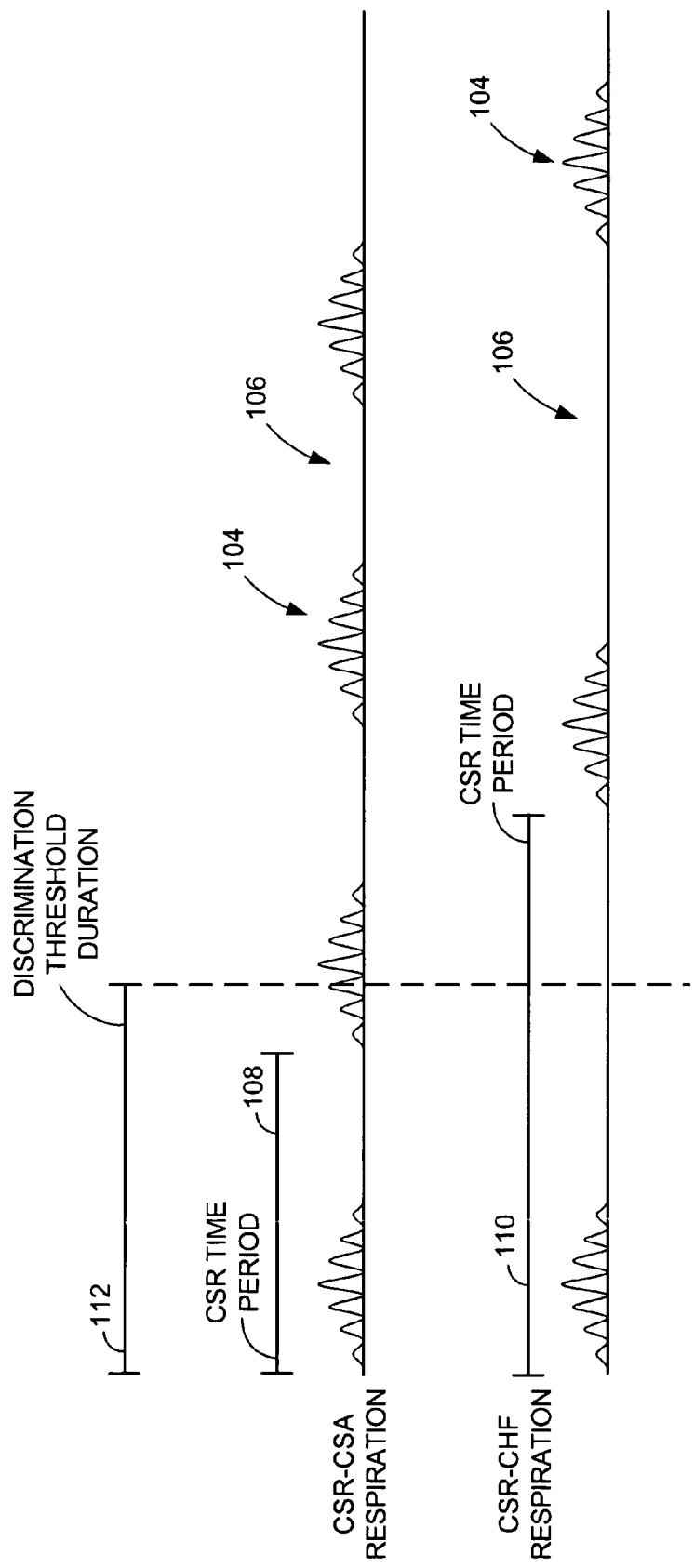
FIG. 3 is a stylized diagram of episodes of CSR illustrating the differences in the CSR periodicity between CSR-CHF and CSR-CSA.

FIG. 3 illustrates exemplary time periods for both CSR-CSA respiration and CSR-CHF respiration. As can be seen, CSR is characterized by intermittent bursts of heavy, deep breathing or hyperpnea 104 separated by periods of sleep apnea 106. Generally speaking, the time period of CSR is the duration from the onset of one breathing cluster to the onset of a next breathing cluster. This time period is also equal to the sum of an apnea time period and the subsequent respiration burst time period. As illustrated, a time period 108 of CSR-CHF is significantly longer than a time period 110 for CSR-CSA. Accordingly, the CSR periodicity provides a basis for discriminating CSR-CSA from CSR-CHF. A discrimination time period threshold duration 112, calculated in accordance with techniques described below, provides a basis for discriminating CSR-CSA from CSR-CHF. If the time period for a particular episode of CSR exceeds the threshold, then the pacer/ICD concludes that it is likely that the episode of CSR was caused by an underlying CHF. Otherwise, it is likely that the episode of CSR is caused by periods of CSA, possibly unrelated to CHF. Alternatively, CSR frequency can instead be evaluated and compared against a CSR frequency discrimination threshold. Also, note that the CSR respiration patterns shown in FIG. 3 are stylized so as to more clearly illustrate pertinent features the respiration patterns and should not be construed as representing actual clinically-detected CSR respiration patterns.

Returning to FIG. 2, the pacer/ICD compares the CSR periodicity, at step 112, for the episode of CSR against the appropriate discrimination threshold to identify the source of the episode of CSR. Then, at step 114, appropriate therapy is delivered and diagnostic data is recorded. As already explained, various types of therapy may be delivered, alone or in combination, depending upon the capabilities of the implanted system. Note that, for most patients, episodes of CSR either are all the result of an underlying CHF or are all the result of periodic episodes of CSA. Hence, once a determination has been made as to whether the patient is suffering from CSR-CSA or CSR-CHF, this determination need not be repeated, at least in the short-term. Accordingly, from many patients, once the source of CSR has been identified, it is sufficient to evaluate additional episodes of CSR only infrequently (e.g. every few weeks or months) to determine a change in status of the patient. In one example, the pacer/ICD analyzes all episodes of CSR for several weeks and, if all are caused by the same underlying source, the pacer/ICD switches its mode of operation to only analyze CSR episodes every few weeks to verify that the episodes are still all caused by the same underlying source. If the patient ultimately begins to develop mixed episodes of CSR, then the pacer/ICD switches its mode of operation to again analyze each individual episode of CSR to identify its particular cause so that appropriate diagnostic information may be stored and appropriate therapy may be delivered. A determination can be made, for example, whether a majority of the episodes of CSR are caused by CSA or caused by CHF and therapy adjusted accordingly. Specific strategies for delivering therapy are set forth below.

Thus, FIGS. 2–3 provide an overview of the CSR discrimination technique of the invention. In the following, an overview of the CHF severity evaluation technique is provided.

Overview of CHF Severity Evaluation Technique

Figure 4:
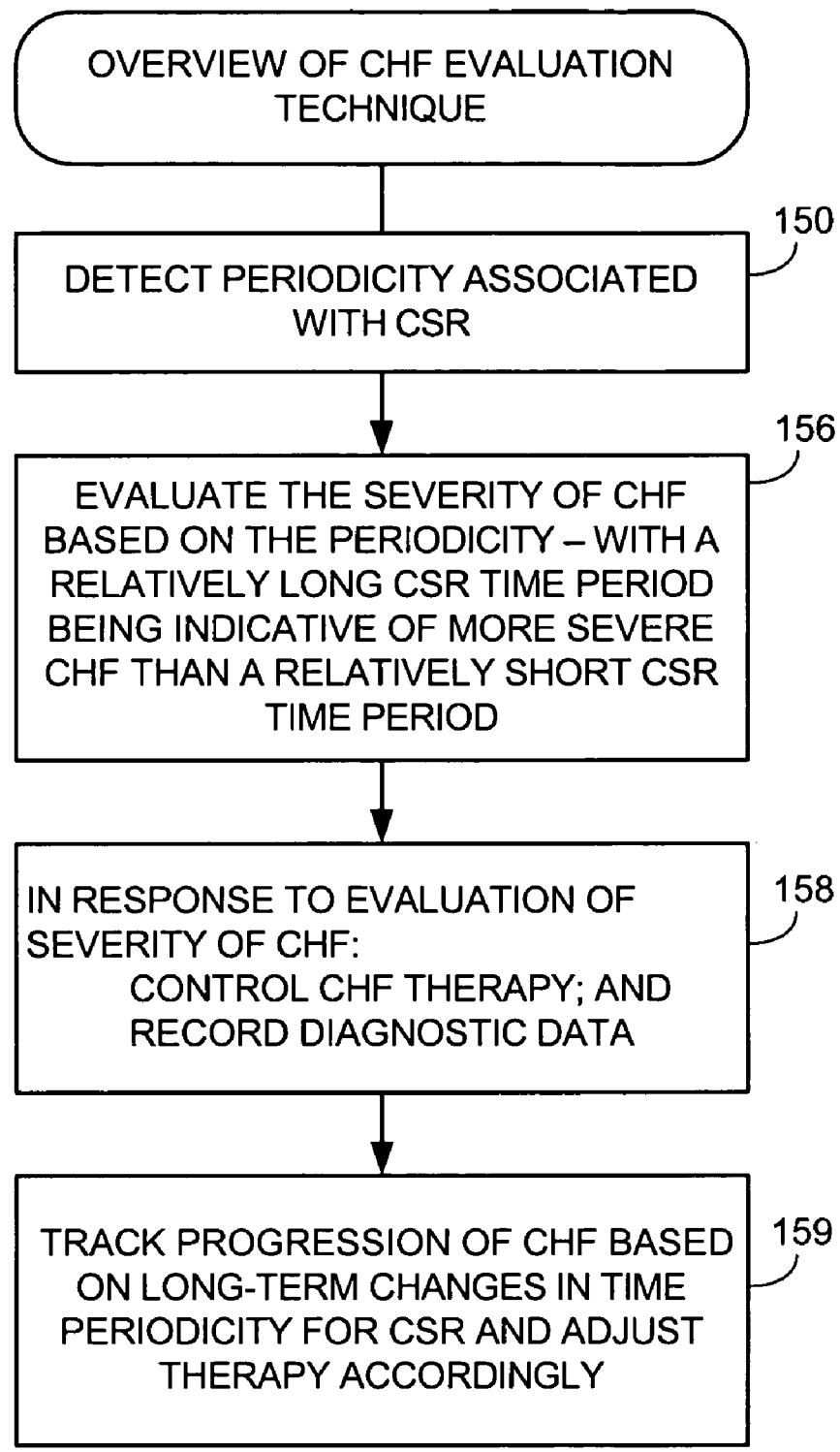
FIG. 4 is a flow diagram providing an overview of the method for tracking severity of CHF based on CSR periodicity as performed by the system of FIG. 1.

FIG. 4 provides an overview of the CHF severity evaluation technique of the invention. The technique may be performed in addition to the CSR discrimination technique of FIG. 2 or may be implemented independently. Beginning at step 150, the pacer/ICD detects a periodicity associated with the CSR for the patient. The patient need not be asleep. Should episodes of CSR occur while the patient is awake, as commonly happens in patients with fairly severe CHF, the severity of CHF may be evaluated based upon such episodes. If CSR only occurs while the patient is asleep, then the evaluation of the severity of CHF is made based upon CSR episodes occurring while asleep.

Figure 5:
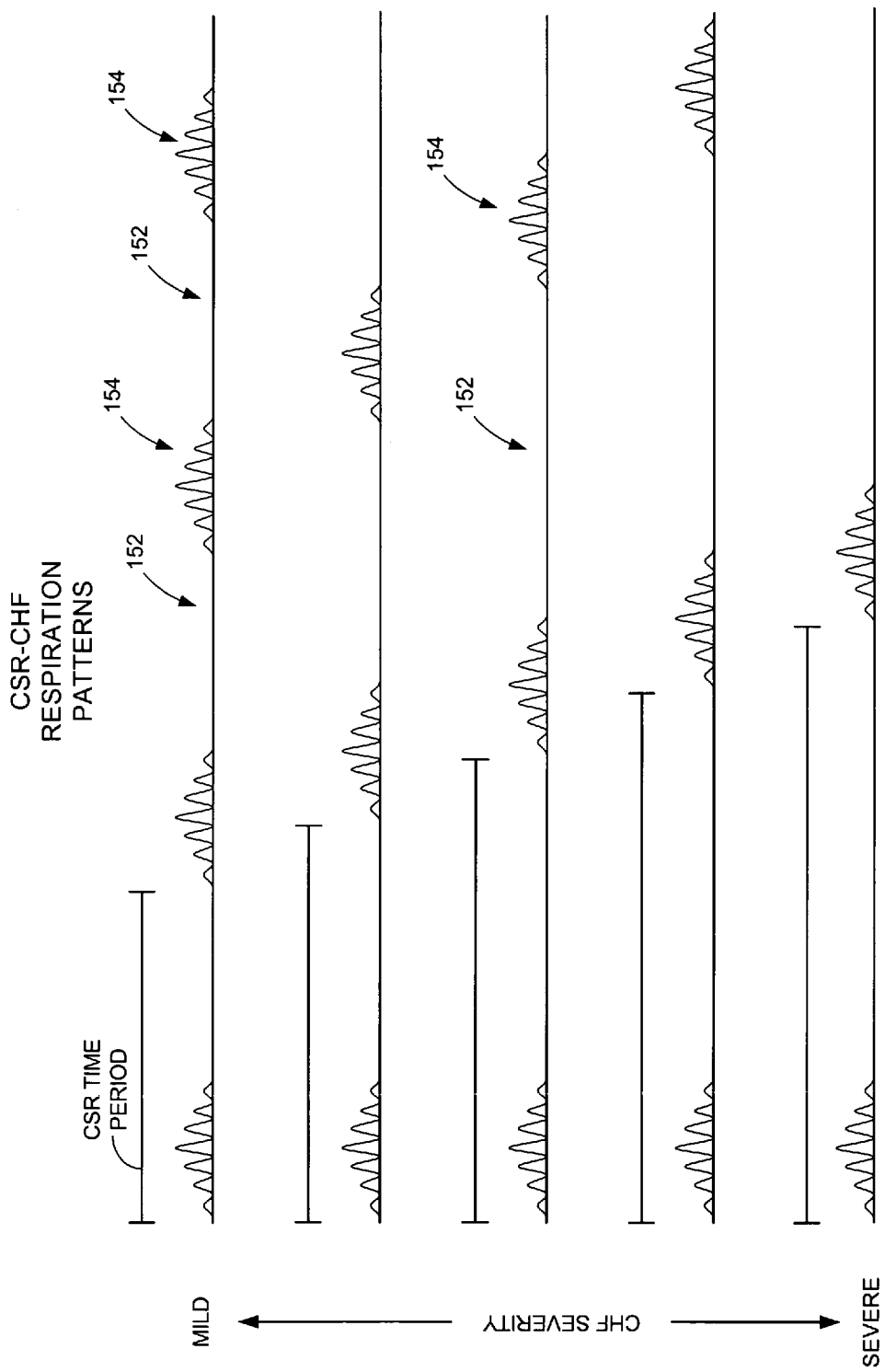
FIG. 5 is a stylized diagram of episodes of CSR illustrating the increase in CHF severity associated with an increase in CSR time period for CSR-CHF.

FIG. 5 illustrates CSR time periods for CSR-CHF respiration patterns for various levels of CHF severity ranging from mild to severe. Again, each CSR respiratory pattern includes alternating periods of apnea 152 followed by brief bursts of hyperpnea 154. As can be seen, CSR time periods are comparatively shorter for patients with mild CHF and considerably longer for patients with more severe CHF. This occurs because circulation delays caused by poor cardiac function due to CHF result in longer feedback loops between the time when the respiratory control centers of the brain sense changes in blood chemistry and the time when those changes in blood chemistry actually occur in the lungs. The longer periods of apnea occurring within patients with severe CHF result in far more significant variations in blood chemistry levels, which tend to exacerbate CHF as well as other medical conditions. In any case, by determining the periodicity for CSR, the severity of CHF can thereby be evaluated. Note that the CSR respiration patterns shown in FIG. 5 are stylized so as to more clearly illustrate pertinent features the respiration patterns and should not be construed as representing actual clinically-detected CSR respiration patterns.

Returning to FIG. 4, the evaluation of CHF severity is performed at step 156 based upon the CSR periodicity detected at step 150—with long CSR time periods being indicative of severe CHF and relatively short time periods being indicative of mild CHF (or with low CSR frequency being indicative of sever CHF and relatively high CSR frequency being indicative of mild CHF.) As explained below, a look-up table of ranges of periodicity values may be accessed, which correspond to the various levels of CHF severity. In any case, once the severity of CHF has been evaluated then, at step 158, CHF therapy is delivered based upon the severity of CHF and appropriate diagnostic data is recorded. Values indicative of the severity of CHF are preferably stored within the pacer/ICD so that the progression of CHF may be tracked, at step 159, over an extended period of time, within increasing values for the CSR time period indicative of progression of CHF. As the disease progresses, the pacer/ICD automatically adjusts CHF therapy by, for example, adjusting CRT control parameters or titrating dosages of any medications automatically delivered via the implanted drug pump. Typically, the severity of CHF does not change significantly over a few days or weeks and hence it is usually sufficient for the pacer/ICD to evaluate the severity of CHF at most only once every few weeks. To ensure that any short term changes in patient status to not improperly affect the tracking of CHF progression, periodicity values for CSR-CHF are averaged over a relatively large number of CSR episodes occurring under similar conditions. In one example, only episodes of CSR occurring while the patient is asleep are employed for use in generating an average periodicity value for CHF severity evaluation. In another example, only episodes of CSR occurring while the patient is awake are employed.

Thus, the FIGS. 4–5 provide an overview of the CSR-CHF severity evaluation techniques of the invention. In the following section, an exemplary pacer/ICD will be described, which includes components for performing the CSR discrimination technique of FIGS. 2–3 as well as the CHF severity evaluation technique of FIGS. 4–5.

Pacer/ICD

Figure 7:
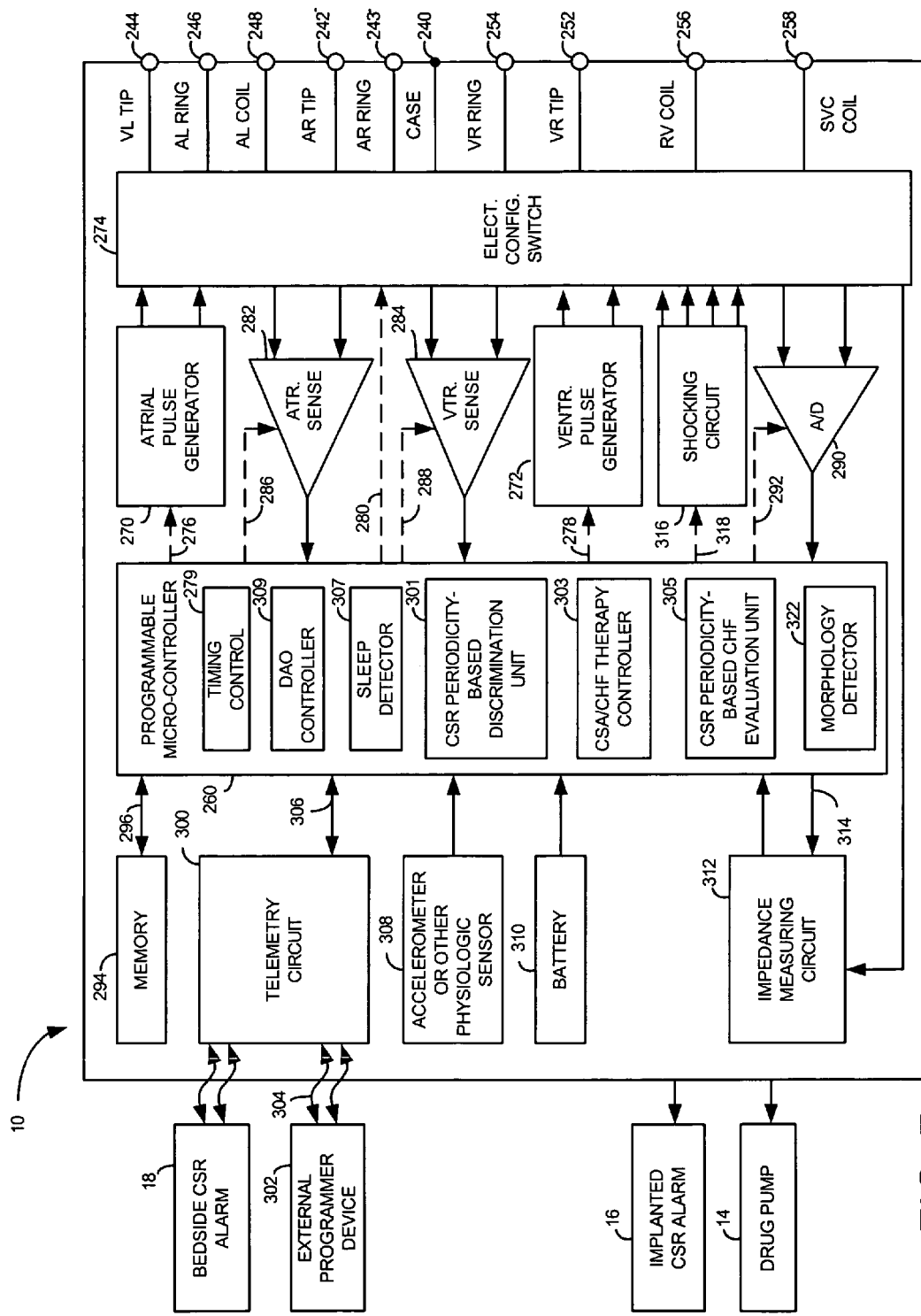
FIG. 7 is a functional block diagram of the pacer/ICD of FIG. 6, illustrating basic circuit elements that provide cardioversion, defibrillation and/or pacing stimulation in four chambers of the heart and particularly illustrating components for distinguishing CSR-CSA from CSR-CHF and for controlling delivery of therapy in response thereto and for tracking the severity of CHF.

With reference to FIGS. 6 and 7, a detailed description of the pacer/ICD of FIG. 1 will now be provided. FIG. 6 provides a simplified block diagram of the pacer/ICD, which is a dual-chamber stimulation device capable of treating both fast and slow arrhythmias with stimulation therapy, including cardioversion, defibrillation, and pacing stimulation, as well as capable of detecting CSR, discriminating CSR-CSA from CSR—CHF, evaluating the severity of CHF based on CSR-CHF, and controlling delivering of therapy in response thereto.

To provide atrial chamber pacing stimulation and sensing, pacer/ICD 10 is shown in electrical communication with a heart 212 by way of a left atrial lead 220 having an atrial tip electrode 222 and an atrial ring electrode 223 implanted in the atrial appendage. Pacer/ICD 10 is also in electrical communication with the heart by way of a right ventricular lead 230 having, in this embodiment, a ventricular tip electrode 232, a right ventricular ring electrode 234, a right ventricular (RV) coil electrode 236, and a superior vena cava (SVC) coil electrode 238. Typically, the right ventricular lead 230 is transvenously inserted into the heart so as to place the RV coil electrode 236 in the right ventricular apex, and the SVC coil electrode 238 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 224 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 224 is designed to receive atrial and ventricular cardiac signals and to deliver left ventricular pacing therapy using at least a left ventricular tip electrode 226, left atrial pacing therapy using at least a left atrial ring electrode 227, and shocking therapy using at least a left atrial coil electrode 228. With this configuration, biventricular pacing can be performed. Although only three leads are shown in FIG. 6, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 7. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 240 for pacer/ICD 10, shown schematically in FIG. 7, is often referred to as the "can", "case" or "case electrode" and may be programmably selected to act as the return electrode for all "unipolar" modes. The housing 240 may further be used as a return electrode alone or in combination with one or more of the coil electrodes, 228, 236 and 238, for shocking purposes. The housing 240 further includes a connector (not shown) having a plurality of terminals, 242, 243, 244, 246, 248, 252, 254, 256 and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 222 and a right atrial ring ($A_R$ RING) electrode 243 adapted for connection to right atrial ring electrode 223. To achieve left chamber sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection to the left ventricular ring electrode 226, the left atrial tip electrode 227, and the left atrial coil electrode 228, respectively. To support right chamber sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 232, right ventricular ring electrode 234, the RV coil electrode 236, and the SVC coil electrode 238, respectively.

At the core of pacer/ICD 10 is a programmable microcontroller 260, which controls the various modes of stimulation therapy. As is well known in the art, the microcontroller 260 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design and operation of the microcontroller 260 are not critical to the invention. Rather, any suitable microcontroller 260 may be used that carries out the functions described herein. The use of microprocessor-based control circuits for performing timing and data analysis functions are well known in the art.

As shown in FIG. 7, an atrial pulse generator 270 and a ventricular pulse generator 272 generate pacing stimulation pulses for delivery by the right atrial lead 220, the right ventricular lead 230, and/or the coronary sinus lead 224 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry (not separately shown) used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 282 and ventricular sensing circuits 284 may also be selectively coupled to the right atrial lead 220, coronary sinus lead 224, and the right ventricular lead 230, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers or shared amplifiers. The switch 274 determines the "sensing polarity" of the cardiac signal by selectively closing the appropriate switches, as is also known in the art. In this way, the clinician may program the sensing polarity independent of the stimulation polarity. Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity in the appropriate chambers of the heart.

For arrhythmia detection, pacer/ICD 10 utilizes the atrial and ventricular sensing circuits, 282 and 284, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 260 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 302. The data acquisition system 290 is coupled to the right atrial lead 220, the coronary sinus lead 224, and the right ventricular lead 230 through the switch 274 to sample cardiac signals across any pair of desired electrodes. The microcontroller 260 is further coupled to a memory 294 by a suitable data/address bus 296, wherein the programmable operating parameters used by the microcontroller 260 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 294 through a telemetry circuit 300 in telemetric communication with the external device 302, such as a programmer, transtelephonic transceiver or a diagnostic system analyzer. The telemetry circuit 300 is activated by the microcontroller by a control signal 306. The telemetry circuit 300 advantageously allows intracardiac electrograms and status information relating to the operation of pacer/ICD 10 (as contained in the microcontroller 260 or memory 294) to be sent to the external device 302 through an established communication link 304. Pacer/ICD 10 further includes an accelerometer or other physiologic sensor 308, commonly referred to as a "rate-responsive" sensor because it is typically used to adjust pacing stimulation rate according to the exercise state of the patient. However, the physiological sensor 308 may further be used to detect changes in cardiac output, changes in the physiological condition of the heart, or diurnal changes in activity (e.g., detecting sleep and wake states) and to detect arousal from sleep. Accordingly, the microcontroller 260 responds by adjusting the various pacing parameters (such as rate, AV Delay, V—V Delay, etc.) at which the atrial and ventricular pulse generators, 270 and 272, generate stimulation pulses. While shown as being included within pacer/ICD 10, it is to be understood that the physiologic sensor 308 may also be external to pacer/ICD 10, yet still be implanted within or carried by the patient. A common type of rate responsive sensor is an activity sensor incorporating an accelerometer or a piezoelectric crystal, which is mounted within the housing 240 of pacer/ICD 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient an, in particular, is capable of detecting arousal from sleep or other movement.

The pacer/ICD additionally includes a battery 310, which provides operating power to all of the circuits shown in FIG. 7. The battery 310 may vary depending on the capabilities of pacer/ICD 10. If the system only provides low voltage therapy, a lithium iodine or lithium copper fluoride cell may be utilized. For pacer/ICD 10, which employs shocking therapy, the battery 310 must be capable of operating at low current drains for long periods, and then be capable of providing high-current pulses (for capacitor charging) when the patient requires a shock pulse. The battery 310 must also have a predictable discharge characteristic so that elective replacement time can be detected. Accordingly, pacer/ICD 10 is preferably capable of high voltage therapy and appropriate batteries.

As further shown in FIG. 7, pacer/lCD 10 is shown as having an impedance measuring circuit 312 which is enabled by the microcontroller 260 via a control signal 314. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 260 further controls a shocking circuit 316 by way of a control signal 318. The shocking circuit 316 generates shocking pulses of low (up to 0.5 joules), moderate (0.5–10 joules) or high energy (11 to 40 joules), as controlled by the microcontroller 260. Such shocking pulses are applied to the heart of the patient through at least two shocking electrodes, and as shown in this embodiment, selected from the left atrial coil electrode 228, the RV coil electrode 236, and/or the SVC coil electrode 238. The housing 240 may act as an active electrode in combination with the RV electrode 236, or as part of a split electrical vector using the SVC coil electrode 238 or the left atrial coil electrode 228 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 260 is capable of controlling the synchronous or asynchronous delivery of the shocking pulses.

Microcontroller 260 also includes various components directed to the detection and treatment of CSR-CSA or CSR-CHF. More specifically, the microcontroller includes a CSR periodicity-based discrimination unit 301 for distinguishing CSR-CSA from CSR-CHF. A CSA/CHF therapy controller 303 delivers appropriate therapy in response to the determination. If the CSR is caused by CHF, a CSR periodicity-based CHF evaluation unit 305 operates to evaluate the severity of CHF, so that appropriate diagnostic information can be stored within memory 294 and so that CHF therapy can be properly controlled based upon the degree of severity. The CSR discrimination unit preferably operates only while the patient is asleep, as detected by a sleep detector 307. Additionally, in response to individual episodes of CSR, therapy controller 303 can control implanted CSR alarm 14 or bedside alarm 18 to deliver appropriate warning or alarm signals to awaken the patient, in an effort to terminate the episode of CSR. If the patient is found to suffer from chronic CSR-CSA or CSR-CHF, DAO pacing may be delivered in attempt to prevent the onset of additional episodes of CSR using DAO controller 309. In addition, implantable drug pump 14 may be activated to deliver medications appropriate for the treatment of CSA or CHF. The operation of these components will be described in detail below with reference to FIG. 4. Finally, note that, although several of these internal components are shown as being sub-components of the microcontroller, some or all may be implemented separately from the microcontroller. Depending upon the implementation, the various components of the microcontroller may be separate software modules. The modules may be combined so as to permit a single module to perform multiple functions.

CSR Discrimination Unit and CHF Tracking Unit

Figure 8:
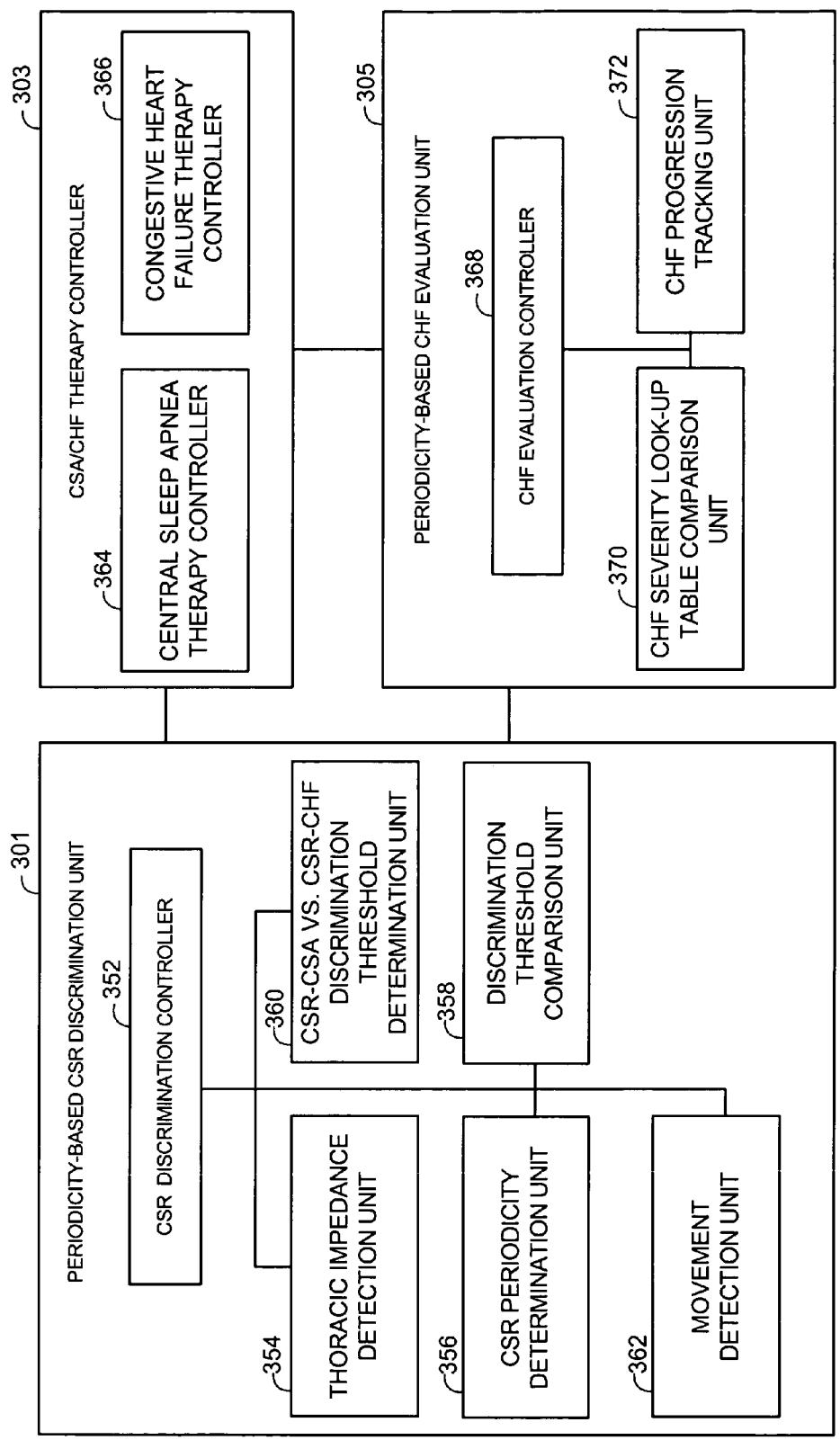
FIG. 8 is a functional block diagram of selected components of the pacemaker or ICD of FIG. 7, particularly illustrating a CSR periodicity-based CSR discrimination unit, a CSA/CHF therapy controller and a CSR periodicity-based CHF evaluation unit.

Pertinent internal functional components of discrimination unit 301, therapy controller 303, and evaluation unit 305 are shown in FIG. 8. Discrimination unit 301 includes a CSR discrimination controller 350, which controls various components directed to the determination of whether episodes of CSR are caused by CSA or CHF. To this end, the controller activates a thoracic impedance detection unit 354, which tracks variations in thoracic impedance caused by respiration based upon signals received from one or more of the leads shown in FIG. 6. As explained more fully below, the impedance detection unit preferably includes internal filters for filtering out non-respiration-based variations in thoracic impedance, such as those caused by the beating of the heart. In any case, a CSR periodicity determination unit 356 is employed to determine the time period or frequency associated with a particular episode of CSR, using techniques also described in detail below. Once the periodicity has been determined, a discrimination threshold comparison unit 358 compares the periodicity against a CSR-CSA vs. CSR-CHF discrimination threshold to identify the source or cause of the particular episode of CSR. The threshold itself is initially determined by a threshold determination unit 360 based upon an analysis of previously-detected respiratory signals. Finally, a movement detection unit 362 determines whether the patient is aroused from sleep or otherwise moves significantly during the discrimination process. This determination may employ physiologic sensor 308 of FIG. 7, which, as noted, may be an accelerometer. In any case, if the patient is aroused during episode of CSR or otherwise moves significantly in such a way that the periodicity associated with CSR is significantly affected, then the discrimination process is deferred until the patient again falls asleep or stops moving so that the periodicity can be reliably determined. An exemplary method used by the components of the CSR discrimination unit to discriminate CSR-CSA from CSR-CHF is described below connection with FIGS. 9–11.

Turning now to therapy controller 303, the controller includes two components: a CSA therapy controller 364 and a CHF therapy controller 366; If CSR is caused by CSA, then the CSA therapy controller delivers appropriate therapy, in a manner described below primarily in connection with FIG. 12. If instead caused by CHF, then the CHF therapy controller instead of deliver appropriate CHF therapy, in a manner described below primarily in connection with FIG. 13.

CHF evaluation unit 305 includes an evaluation controller 368. The evaluation controller activates a CHF severity lookup table comparison unit 370 to compare the CSR periodicity value detected by unit 356 of the discrimination unit 301 with a set of look-up table values stored within memory 294. This is explained in greater detail below with reference to FIG. 14. A CHF progression tracking unit 372 tracks the progression of CHF over an extended period of time based on long-term changes in average CSR periodicity. This too is described below in connection with FIG. 14.

Thus, FIG. 8 summarizes the internal functional components of discrimination unit 301, therapy controller 303 and evaluation unit 305. Depending upon the implementation, the components may be configured as separate software or hardware modules. The modules may be combined so as to permit single modules to perform multiple functions.

Exemplary CSR Discrimination Technique

Figure 9:
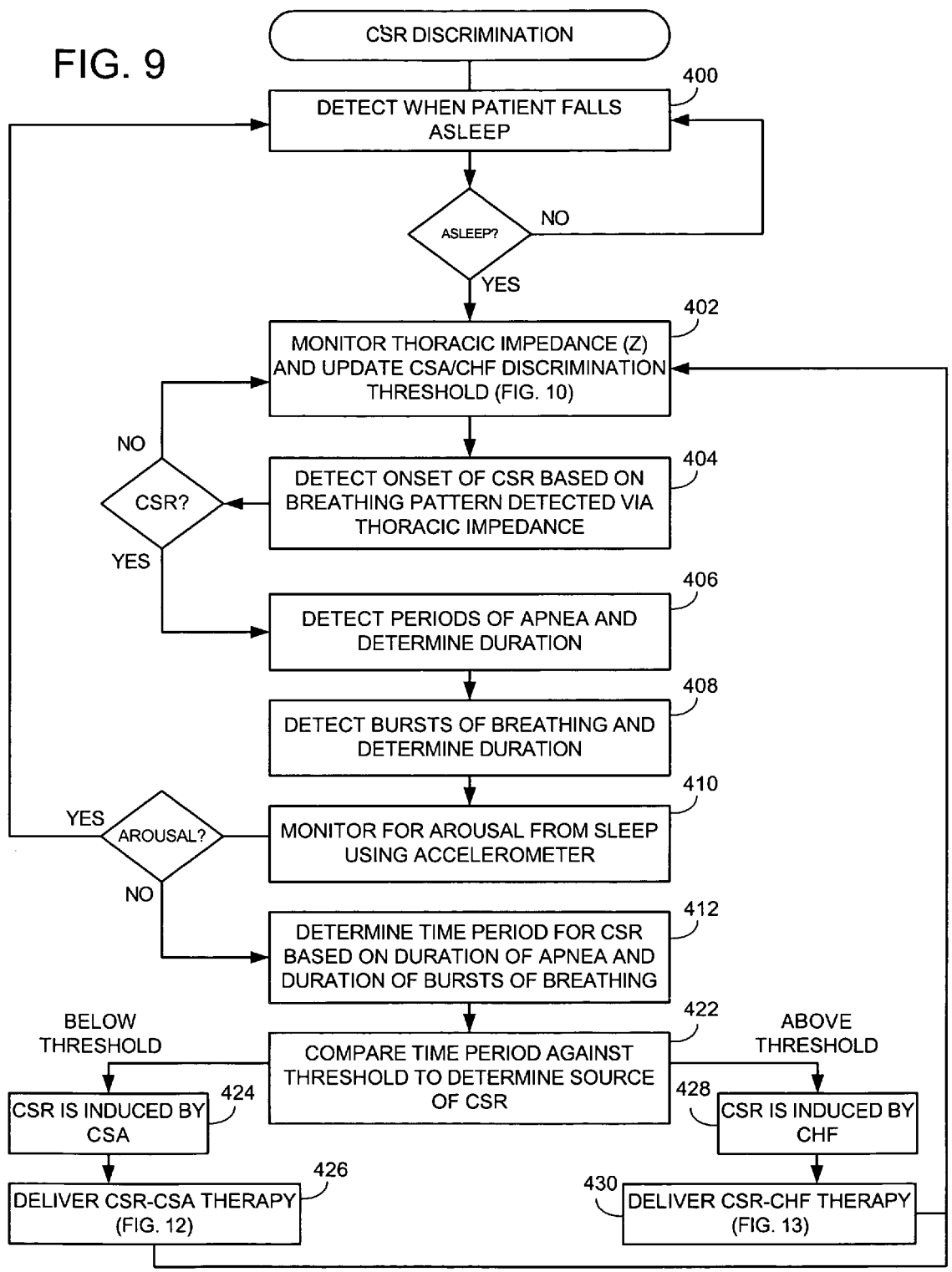
FIG. 9 is a flow diagram illustrating an exemplary method performed by the implanted device of FIG. 7 for distinguishing CSR-CSA from CSR-CHF based on a CSR time period derived from monitoring thoracic impedance.

One particular example of a CSR discrimination technique that may be performed using the systems described above is set forth in FIGS. 9–13. Referring first to FIG. 9, at step 400, the pacer/ICD detects when the patient falls asleep. Any of a variety of otherwise conventional sleep detection techniques may be employed. Examples are set forth in the following patents or patent applications: U.S. Pat. No. 5,476,483, to Bornzin et al., entitled "System and Method for Modulating the Base Rate During Sleep for a Rate-responsive Cardiac Pacemaker"; U.S. Pat. No. 6,128,534 to Park et al., entitled "Implantable Cardiac Stimulation Device And Method For Varying Pacing Parameters To Mimic Circadian Cycles "; and in U.S. patent application Ser. No.

10,339,989 of Koh et al., entitled "System And Method For Detecting Circadian States Using An Implantable Medical Device", filed Jan. 10, 2003.

Once the patient has fallen asleep then, at step 402, the pacer/ICD begins track thoracic impedance (Z), at step 402. Thoracic impedance may be detected using any of a variety of otherwise conventional techniques. An example is set forth the U.S. Pat. No. 5,817,135 to Cooper, et al. entitled, "Rate-Responsive Pacemaker with Noise-Rejecting Minute Volume Determination". Preferably, the thoracic impedance values are filtered to eliminate variation in impedance caused by the beating of the heart or other non-respiratory factors. In one example, a low pass filter is employed having a cutoff frequency set to some value greater than the frequency of respiratory breathing but less than the frequency associated with the beating heart. For example, a cutoff frequency of 30 cycles per minute may be employed. In addition, at step 402, the pacer/ICD updates a previously-determined discrimination threshold using a technique described below in connection with FIG. 11. If a discrimination threshold has not yet been calculated, a default value is instead employed, such as a value in the range of 30 to 40 seconds.

At step 404, pacer/ICD detects the onset of an episode of CSR based upon breathing patterns detected via thoracic impedance and any of a variety of otherwise conventional CSR detection techniques can be employed, which exploit thoracic impedance. Alternatively, other techniques may be employed such as techniques exploiting variations in A-V delay or R—R oscillations. Examples of CSR detection techniques are discussed in U.S. Pat. No. 6,600,949 to Turcott and in U.S. Pat. No. 6,589,188 Street, et al., which are incorporated by reference herein. Assuming CSR has been detected then, at step 406, the pacer/ICD detects periods of sleep apnea occurring within CSR and determines their duration. At step 408, bursts of breathing (i.e. hyperpnea) occurring during CSR are detected and their durations are also measured. Preferably, the apnea durations and the hyperpnea durations are averaged over several cycles during CSR. While apnea and hyperpnea durations are being tracked, the pacer/ICD also monitors for arousal from sleep (or significant movement) using the accelerometer, at step 410, and, if arousal is detected, the CSR discrimination process is aborted and processing instead returns to step 400 to again await detection of another sleep state. In this manner, potentially erroneous apnea and hyperpnea durations are discarded so that the values do not improperly influence the determination of whether CSR is caused by CSA or CHF. In any case, assuming that the patient is still asleep then, at step 412, the pacer/ICD determines the time period for the episode of CSR and based upon the average durations of apnea and the average durations of hyperpnea occurring following the periods of apnea.

FIG. 10 illustrates filtered impedance (denoted LP-Z) for an exemplary episode of CSR. As can be seen, changes in impedance reveal bursts of hyperpnea 414 following each period of apnea 416. The duration of a period of apnea is identified by bracketed portion 418. The duration of a period of hyperpnea is indicated by bracketed portion 420. The sum of the hyperpnea duration and the apnea duration collectively define the time period for CSR. A burst of hyperpnea may be identified, for example, by specifying an impedance variation threshold, above which hyperpnea is presumed. If the variation in impedance remains below that threshold, apnea is presumed. This respiration detection threshold differs from the CSR discrimination threshold, discussed elsewhere herein. In any case, during an episode of CSR, time periods for at least a few cycles of apnea/hyperpnea are tracked so as to provide an average time period value.

Returning to FIG. 9, at step 422, the CSR time period is compared against the discrimination threshold updated at step 402 to identify the source of the particular episode of CSR. If the time period is below the discrimination threshold, then the episode of CSR is deemed to have been caused by CSA (step 424) and CSR-CSA therapy is initiated, at step 426. Otherwise, if the time period exceeds the determination threshold then CSR is deemed to have been caused by CHF (at step 428) and CSR-CHF therapy is initiated at step 430. After steps 426 or 430, processing resumes at step 402 to detect the onset of any additional episodes of CSR occurring while the patient is still asleep so that the cause of any such episodes can also be determined. As noted above, some patients are subject to both CSR-CSA and CSR-CHF and so it is desirable to identify the source of each episode of CSR.

Hence, FIG. 9 illustrates an exemplary method for discriminating CSR-CSA from CSR-CHF based upon CSR time periods as determined based upon a separate calculation of apnea time periods and hyperpnea time periods. Alternative techniques may instead be employed for detecting the time period. For example, the duration from one hyperpnea burst to another may instead be employed by, for example, detecting the peak or midpoint of consecutive breathing bursts. However, separate detection of the durations of the apnea time periods and the hyperpnea time periods is believed to be more reliable and hence is preferred. In addition, frequency values for CSR can instead be exploited.

Figure 11:
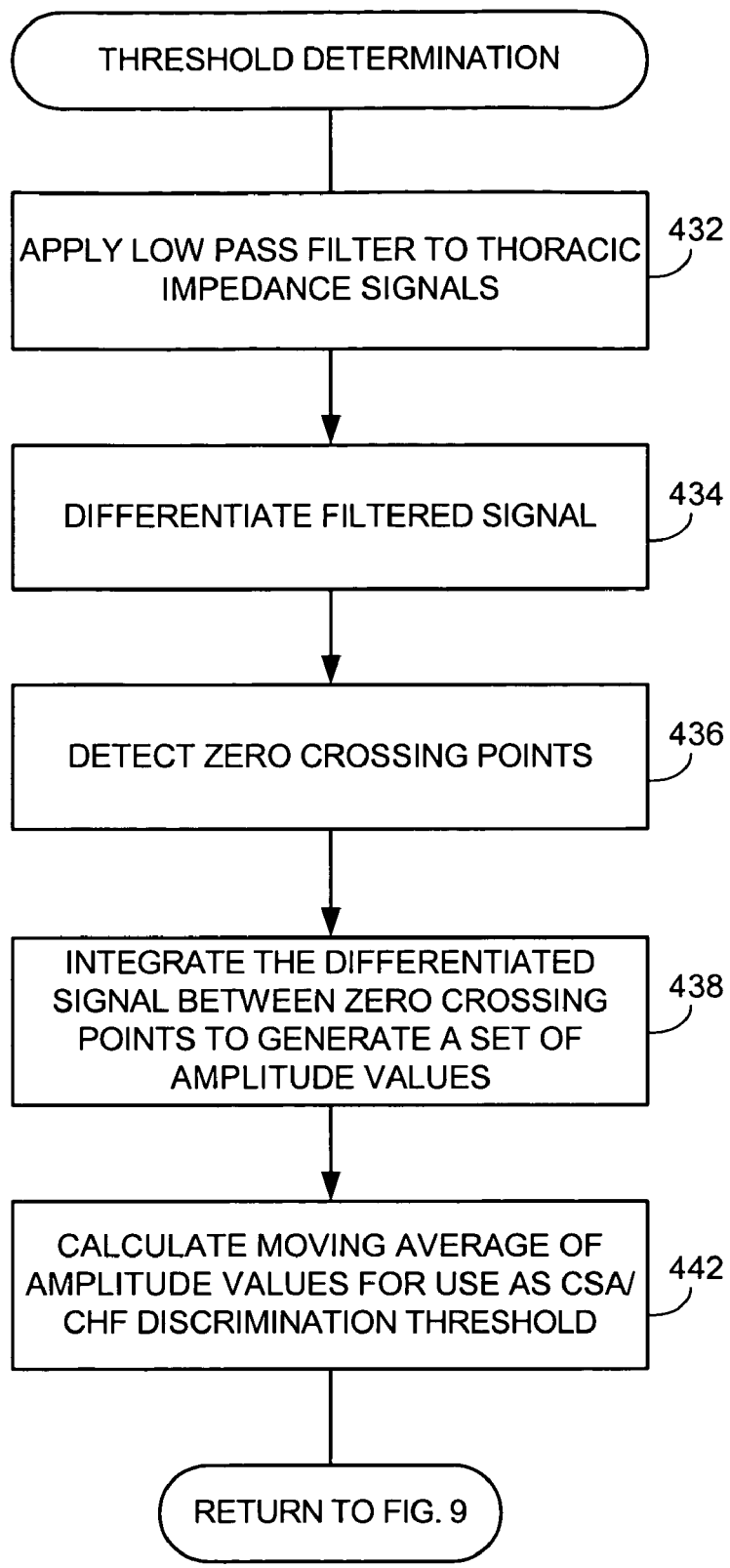
FIG. 11 is a flow diagram illustrating an exemplary method performed by the implanted device of FIG. 7 for determining a CSR time period discrimination threshold for use in the method of FIG. 9.

Referring now to FIG. 11, an exemplary technique for determining and updating the discrimination threshold will now be described for use during step 402 of FIG. 9. Initially, at step 432, a low pass filter is applied to the thoracic impedance signals (if the impedance signals have not already in filtered) to eliminate variations caused by the beating of the heart or other non-respiratory factors. The resulting filtered impedance signal is illustrated in FIG. 10 and has already been discussed. Then, at step 434, the filtered impedance signal is differentiated, i.e. the mathematical derivative of the filtered signal is calculated, herein denoted dZ. With the filtered impedance signal represented internally by digital values, standard digital techniques are employed to calculate (dZ). The differentiated signal dZ is shown in FIG. 10 as graph 436. Next, at step 436, zero crossing points are identified within the differentiated signal dZ. The zero crossing points correspond to peaks and valleys within the original filtered impedance signal.

At step 438, the differentiated signal dZ is then integrated between consecutive zero crossing points to generate a set of amplitude values, indicative of valley-to-peak amplitude variations. With dZ represented internally by digital values, standard digital techniques are employed to integrate or sum dZ to generate the individual amplitude values. Individual integrated values are shown within FIG. 10 as graph 440. Each individual value within graph 414 thereby provides a measure of the variation from a negative valley to a next positive peak within the filtered impedance signal. Hence, these values are indicative of the range of physical movement of the thorax from maximum contraction to maximum expansion during a respiration cycle. During apnea, of course, there is little or no variation since the patient is not breathing. During periods of hyperpnea, significant variation occurs. Hence, the integrated values provide a clear indication of periods of hyperpnea and periods of apnea. At step 442, a moving average of the integrated values is calculated. It is this moving average that is used as the CHF discrimination threshold of FIG. 9. The moving average is shown within FIG. 10 as line 444. If the average time period associated with a given episode of CSR clearly exceeds the threshold, CSR-CHF is deemed to be occurring. If the average time period associated with a given episode of CSR is clearly below the threshold, CSR-CSA is deemed to be occurring. If the average value is near the threshold, it is rejected and CSR discrimination is deferred until more average time period values are detected that are clearly above or below the threshold.

Hence, FIGS. 9–11 illustrate one possible technique for calculating a threshold for use in discriminating CSR-CHF from CSR-CSA based upon the periodicity of CSR. Other techniques may alternatively be employed. Note that, since the integrated values of graph 444 of FIG. 10 provide a clear indication of periods of hyperpnea and periods of apnea, the integrated values can additionally be used for calculating the time periods associated with CSR during steps 406–412. For example, periods of hyperpnea may be calculated by determining whether the integrated values exceed a hyperpnea threshold. Likewise, a period of apnea may be detected by determining when the integrated values fall below the hyperpnea threshold.

CSR-CSA and CSR-CHF Therapy

Figure 12:
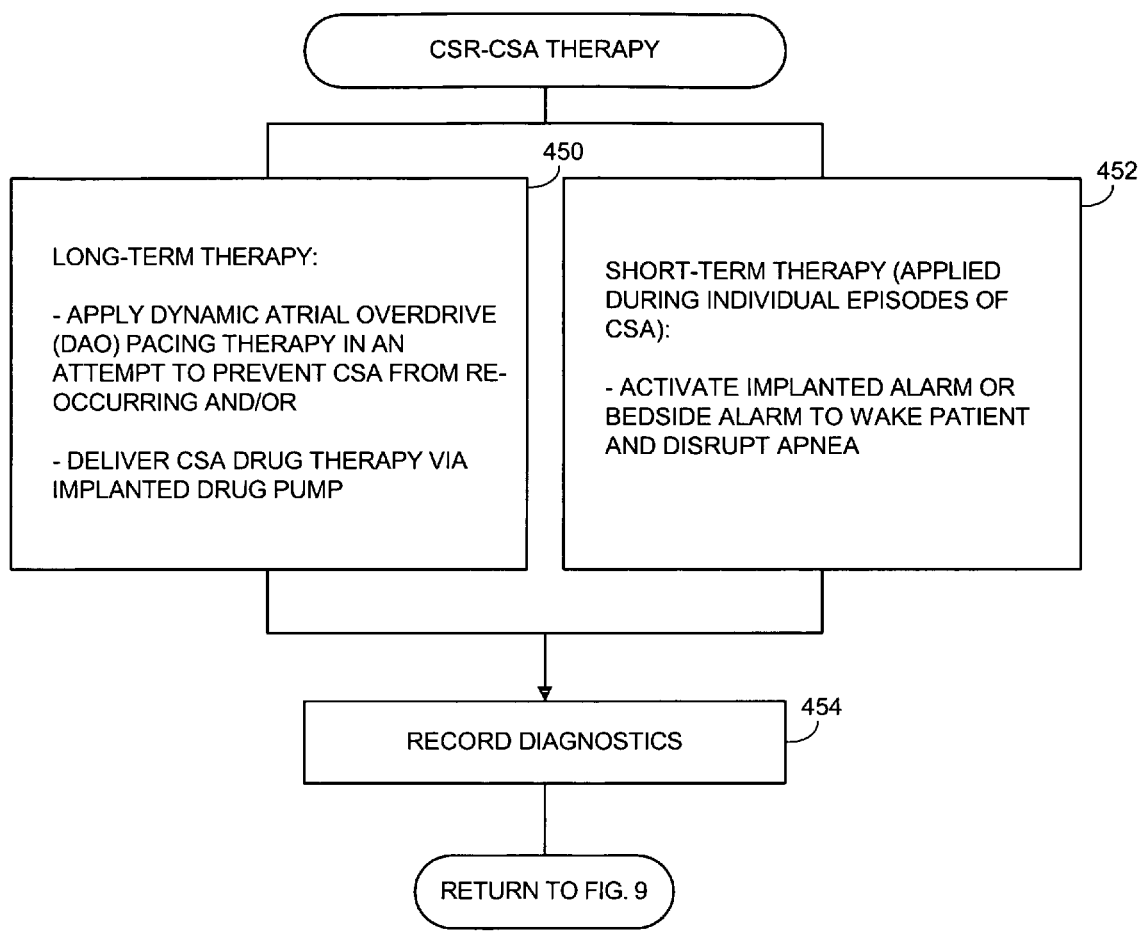
FIG. 12 is a flow diagram illustrating an exemplary method performed by the implanted system of FIG. 7 for delivering therapy in response to a determination that CSR is induced by CSA.

CSR-CSA therapy is summarized in FIG. 12. Two forms of therapy are provided: long-term therapy and short-term therapy. Long-term therapy is preferably employed at all times within patients who are found to be subject to frequent episodes of CSR-CSA. Short-term therapy is applied only during individual episodes of CSR-CSA. Long-term therapy, performed at step 452, includes DAO pacing therapy applied in an attempt to prevent the onset of additional episodes of CSR-CSA. A particularly effective overdrive pacing technique for the atria, referred to herein as dynamic atrial overdrive (DAO) pacing, is described in U.S. Pat. No. 6,519,493 to Florio et al., entitled "Methods And Apparatus For Overdrive Pacing Heart Tissue Using An Implantable Cardiac Stimulation Device". With DAO, the overdrive pacing rate is controlled to remain generally uniform and, in the absence of a tachycardia, is adjusted upwardly or downwardly only occasionally. The aggressiveness of overdrive pacing may be modulated by adjusting the overdrive pacing rate and related control parameters. See: U.S. patent application Ser. Nos. 10/093,225 and 10/092,695, both of Florio et al., entitled "Method And Apparatus For Using A Rest Mode Indicator To Automatically Adjust Control Parameters Of An Implantable Cardiac Stimulation Device", both filed Mar. 6, 2002; U.S. patent application Ser. No. 10/043,781, also of Florio et al., entitled "Method And Apparatus For Dynamically Adjusting A Non-Linear Overdrive Pacing Response Function", filed Jan. 9, 2002; and U.S. patent application Ser. No. 10/043,472, of Florio et al., entitled "Method And Apparatus For Dynamically Adjusting Overdrive Pacing Parameters", filed Jan. 9, 2002. These DAO applications are incorporated by reference herein. Preferably, parameters for controlling DAO therapy are set to values appropriate for reducing the likelihood of additional episodes of CSR-CSA. Routine instrumentation may be performed to identify optimal DAO pacing parameters for use with patients with CSR-CSA. The aggressiveness of DAO therapy may be adjusted based upon the frequency or duration of episodes of CSA occurring during CSR-CSA.

Long-term CSR-CSA therapy also includes the delivery of anti-apnea medications via an implantable drug pump, if so equipped. Examples of medications that may be helpful in patients with apnea are set forth the following patents: U.S. Pat. No. 6,331,536 to Radulovacki, et al., entitled "Pharmacological Treatment for Sleep Apnea"; U.S. Pat. No. 6,432,956 to Dement, et al. entitled "Method for Treatment of Sleep Apneas"; U.S. Pat. No. 6,586,478 to Ackman, et al., entitled "Methods and Compositions for Improving Sleep"; and U.S. Pat. No. 6,525,073 to Mendel, et al., entitled "Prevention or Treatment of Insomnia with a Neurokinin-1 Receptor Antagonist". Depending upon the particular medication, alternative compounds may be required for use in connection with an implantable drug pump. Routine experimentation may be employed to identify medications for treatment of sleep apnea that are safe and effective for use in connection with an implantable drug pump. Dosages may be titrated based upon the frequency or duration of episodes of CSA occurring during CSR-CSA.

Short-term CSR-CSA therapy, performed at step 450, involves triggering an implantable CSR alarm (such as alarm 14 of FIG. 1) to awaken the patient in an attempt to terminate the episode of CSR-CSA. Alternatively, a bedside alarm may be activated by transmission of appropriate wireless control signals. As already noted, activation of an alarm to awaken the patient is preferably employed only if long-term therapy is found to be ineffective, since awakening the patient interrupts with the patient's natural sleeping patterns. In any case, whenever some form of CSA therapy is delivered, appropriate diagnostic information is stored at step 454 so that if medical professional can subsequently review the therapy and evaluate its effectiveness.

If implantable phrenic nerve stimulators are implanted, short-term therapy can also involve delivery of rhythmic electrical stimulation to the phrenic nerves to mimic breathing. Examples of phrenic nerve stimulators are set forth in U.S. Pat. No. 5,056,519 to Vince, entitled "Unilateral Diaphragmatic Pacer" and in U.S. Pat. No. 6,415,183 to Scheiner, et al., entitled "Method and Apparatus for Diaphragmatic Pacing", which are incorporated by reference herein. Other respiratory nerves may be stimulated as well. U.S. Pat. No. 5,911,218 to DiMarco, entitled "Method and Apparatus for Electrical Stimulation of the Respiratory Muscles to Achieve Artificial Ventilation in a Patient" describes stimulation of nerves leading to intercostal muscles.

Figure 13:
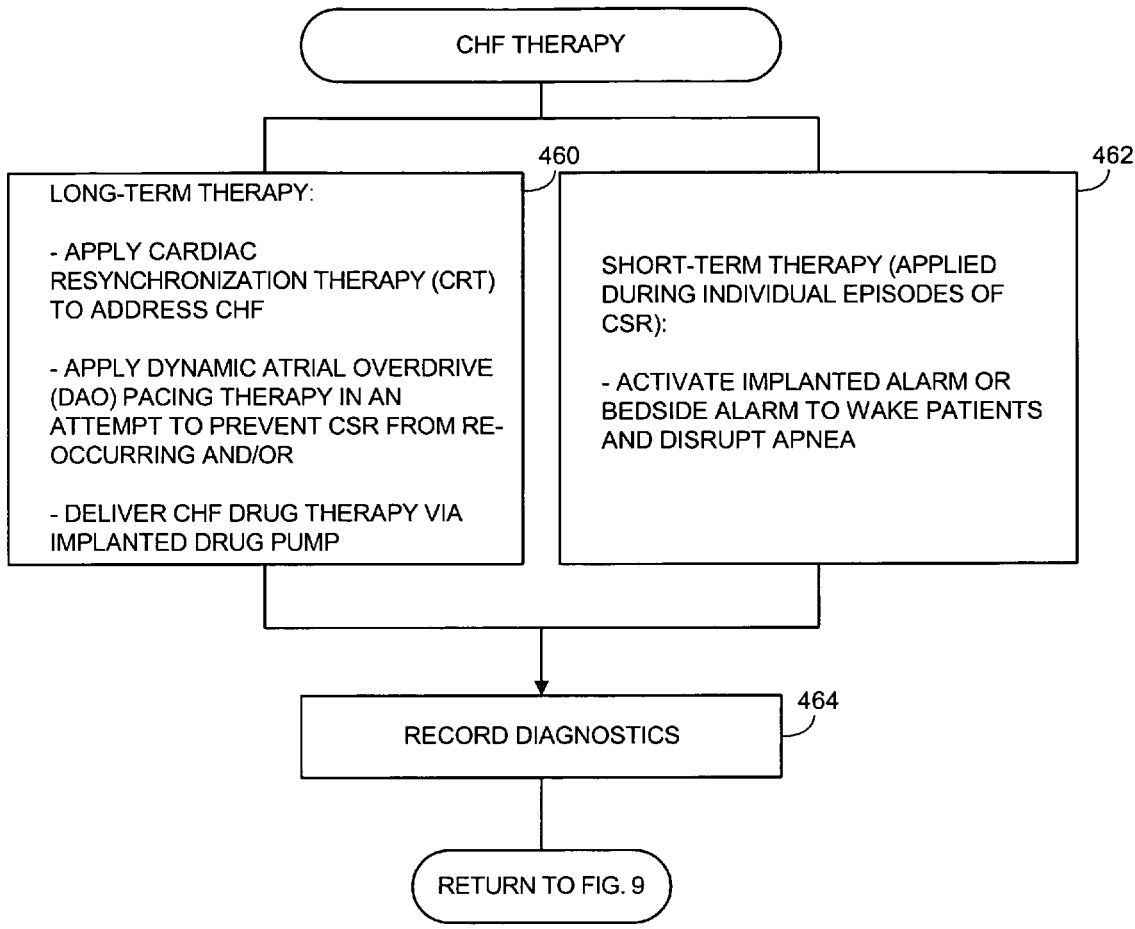
FIG. 13 is a flow diagram illustrating an exemplary method performed by the implanted system of FIG. 7 for delivering therapy in response to a determination that CSR is induced by CHF.

CSR-CHF therapy is summarized in FIG. 13. Again, two forms of therapy are provided: long-term therapy and short-term therapy. Long-term therapy is preferably employed at all times within patients found to be subject to frequent periods of CSR-CHF whereas short-term therapy is applied only during individual episodes of CSR-CHF. Long-term therapy, performed at step 460, may include use of CRT to improve cardiac function. CRT is primarily applied to counteract the debilitating effects CHF but can also be helpful in preventing additional episodes of CSR-CHF. CRT may be performed in accordance with otherwise conventional techniques, such as those set forth in the aforementioned patents to Mathis, et al., Kramer, et al., and Stahmann, et al. Additionally, or in the alternative, DAO pacing therapy is applied in an attempt to prevent the onset of additional episodes of CSR-CHF. Again, preferably, the parameters for controlling DAO therapy are set to values appropriate for reducing the likelihood of additional episodes of CSR-CHF and routine experimentation may be performed to identify such optimal parameters. Note that the specific parameters for controlling DAO therapy to prevent the onset of CSR-CHF may differ from the parameters for controlling DAO to prevent the onset of CSR-CHF. Hence, if a particular patient is only subject to CSR-CHF but not CSR-CSA, a different set of control parameters may be employed than if the patient is subject to both. Long-term CSR-CHF therapy also includes delivery of CHF medications via an implantable drug pump, if so equipped. Exemplary CHF medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of CHF that are safe and effective for use in connection with an implantable drug pump. Dosages may be titrated based upon the frequency or duration of episodes of CSR occurring as a result of CHF.

Short-term CSR-CHF therapy, performed at step 462, includes use of the implantable CSR alarm or external bedside alarm to awaken the patient. Again, activation of an alarm to awaken the patient is preferably employed only if other forms of therapy are found to be ineffective. In any case, whenever some form of CSR-CHF therapy is delivered, appropriate diagnostic information is stored at step 464.

Exemplary CSR Severity Evaluation Technique

One particular example of a CHF severity evaluation technique that may be performed using the systems described above is set forth in the FIG. 14. In this example, the severity of CHF is evaluated based on CSR occurring while patient is asleep and any arousal from sleep during the evaluation process is also detected. In other examples, the severity of CHF may be evaluated based on CSR occurring while the patient is awake. The steps of detecting sleep and monitoring for arousal from sleep are provided for the sake of completeness. In addition, several of the steps are similar to those of the technique of FIG. 9 and, accordingly, such steps are not described again in detail.

Figure 14:
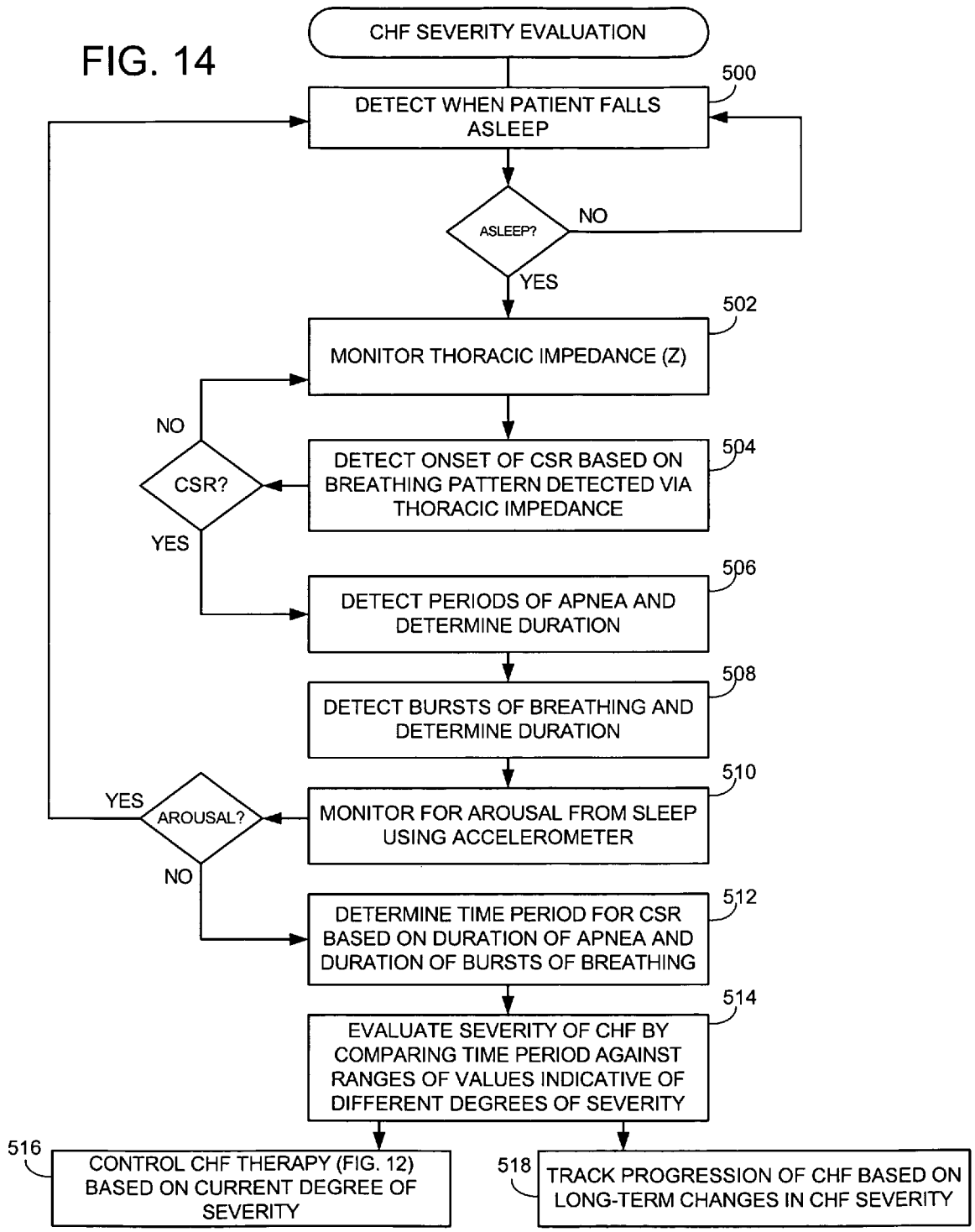
FIG. 14 is a flow diagram illustrating an exemplary method performed by the implanted device of FIG. 7 for evaluating the severity of CHF based on CSR periodicity derived from monitoring thoracic impedance.

At step 500 of FIG. 14, the pacer/ICD detects when the patient falls asleep and then, at step 502, tracks thoracic impedance Z, at step 502. Note that the pacer/ICD need not calculate a discrimination threshold as in FIG. 9. At step 504, the pacer/ICD detects the onset of an episode of CSR using otherwise conventional techniques. Assuming CSR has been detected then, at step 506, the pacer/ICD detects periods of sleep apnea occurring within CSR and then determines their duration and, at step 508, detects bursts of hyperpnea and determines their durations as well. Again, preferably, the apnea durations and the hyperpnea durations are averaged over several cycles during CSR. While apnea and hyperpnea durations are being tracked, the pacer/ICD also monitors for arousal from sleep using the accelerometer, at step 510, and if arousal is detected the CHF severity evaluation process is aborted and processing instead returns to step 500 to again await detection of another sleep state. Assuming that the patient is still asleep then, at step 512, the pacer/ICD determines the time period for the episode of CSR based upon the average durations of apnea and the average durations of hyperpnea. At step 514, the time period is compared against a range of values representative of different degrees of severity of CHF derived for the patient. Preferably, the range of values is set based upon a baseline value of CSR periodicity obtained for the particular patient. For example, if a physician examines the patient and determines that CSR is still mild, the current CSR time period for the patient may then be used as a baseline for specifying ranges values corresponding to mild CSR and corresponding to more severe forms of CSR for the patient.

Exemplary values for a hypothetical patient are set forth in TABLE I. In this example, the baseline periodicity for mild CSR within the patient is in the range of 40 to 50 seconds. From that baseline periodicity, ranges of values corresponding to more severe CSR are specified, so that changes in the severity of CSR may be tracked within the patient. The ranges of values may be specified by the physician or may be generated by the pacer/ICD based upon data input by the physician. For a different patient, a different baseline periodicity may be obtained and different values for the various levels of severity may be specified. The values of TABLE I are hypothetical values provided merely for illustrating the invention. Although only four classifications are showing TABLE I, the severity of CHF may be further subdivided into more additional classification levels. If CSR periodicity is instead calculated based on frequency, then corresponding frequency ranges are instead employed.

TABLE I

| CSR TIME PERIOD (in seconds) | SEVERITY CLASSIFICATION |
|---|---|
| 40–50 | Mild |
| 51–65 | Moderate |
| 61–80 | Severe |
| above 80 | Very Severe |

At step 516, CHF therapy is controlled based upon the degree of severity. CHF therapy is discussed above in connection with FIG. 13. The degree of severity may be used, for example, to control CRT pacing parameters, such as the time delay between left and right ventricular pulses or to control pharmacological CHF therapy to, for example, select the type of pharmacological agents to be delivered via the implantable drug pump or to titrate dosages. At step 518, the pacer/ICD tracks the progression of CHF based on long-term changes in CHF severity, such as changes occurring over weeks or months. To this end, the pacer/ICD stores individual values indicative of CHF severity, such as the CSR time period value, and then periodically compares newly-detected CSR time period values against previous ones to track CHF progression. Appropriate diagnostic information is stored so that a physician can review the data during a follow-up session. If a significant progression in CHF occurs and if the system is so equipped, warning signals can be transmitted to the bedside monitor for immediate relay to the physician, perhaps via telephonic transmission, so that the physician is thereby promptly advised of the change in status.

Hence, FIG. 14 illustrates one possible technique for evaluating the severity of CHF. Others techniques may be performed in accordance with the general principles of the invention.

What have been described are various systems and methods for detecting CSR, distinguishing between CSR-CSA and CSR—CHF, evaluating the severity of CHF based on CSR, and delivering and controlling therapy in response thereto using an implantable system controlled by a pacer or ICD. However, principles of the invention may be exploiting using other implantable systems or in accordance with other techniques. Thus, while the invention has been described with reference to particular exemplary embodiments, modifications can be made thereto without departing from the spirit and scope of the invention.

What is claimed is:

1. A method for distinguishing Cheyne-Stokes Respiration (CSR) within a patient caused by central sleep apnea (CSA) from CSR caused by congestive heart failure (CHF) using an implanted medical device, the method comprising:

detecting a periodicity associated with CSR for the patient; and determining whether the CSR of the patient is caused by CSA or by CHF based on the periodicity.

2. The method of claim 1 wherein detecting the periodicity is performed to detect a time period representative of periodic breathing during CSR.

3. The method of claim 2 wherein detecting a time period associated with CSR for the patient comprises:
   detecting sleep;
   detecting an episode of CSR during sleep; and
   determining the average duration of periods of sleep apnea during CSR, determining the average duration of periods of breathing between the periods of sleep apnea during CSR, combining the average duration of periods of sleep apnea with the average duration of periods of breathing.

4. The method of claim 3 wherein determining the average duration of periods of sleep apnea during CSR and determining the average duration of periods of breathing between the periods of sleep apnea during CSR are performed using on one or more of thoracic impedance, AV delay; R—R oscillations.

5. The method of claim 1 wherein determining whether the CSR of the patient is caused by CSA or by CHF based on the periodicity comprises:
   comparing a time period associated with CSR against a predetermined discrimination threshold, and
   if the time period exceeds the discrimination threshold, generating a signal indicating that the CSR is induced by CHF, otherwise generating a signal indicating that the CSR is induced by CSA.

6. The method of claim 5 and further comprising calculating the discrimination threshold by:
   sensing signals representative of thoracic impedance;
   low pass filtering the impedance signals;
   calculating a derivative of the filtered impedance signal;
   identify zero-crossing points within the derivative of the filtered impedance signal;
   integrating the derivative of the filtered impedance signal between each pair of consecutive zero-crossing points to generate a set of integral values; and
   calculating moving average of integrated values for use as the threshold.

7. The method of claim 5 and further comprising setting the discrimination threshold to an initial value between 30 and 40 seconds.

8. The method of claim 3 further comprising detecting arousal of the patient from sleep and rejecting any determination of the periodicity associated with CSR if arousal from sleep occurred during the episode of CSR.

9. The method of claim 8 wherein detecting arousal of the patient from sleep is performed based on accelerometer signals.

10. The method of claim 1 further comprising recording diagnostic data relevant to the determining of whether the CSR of the patient is caused by GSA or by CHF.

11. The method of claim 1 further comprising determining whether the patient is asleep.

12. The method of claim 11 wherein determining whether the patient is asleep is performed based on patient activity levels or blood carbon dioxide levels.

13. The method of claim 1 further comprising delivering therapy to the patient.

14. The method of claim 1 further comprising delivering electrical nerve stimulation to at least one phrenic nerve of the patient.

15. The method of claim 1 further comprising delivering cardiac resynchronization therapy to the heart of the patient.

16. The method of claim 1 further comprising evaluating the severity of CHF if the CSR of the patient is caused by CHF.

17. The method of claim 16 further comprising delivering therapy to the patient based on the severity of CHF.

18. A system for distinguishing Cheyne-Stokes Respiration (CSR) within a patient caused by central sleep apnea (CSA) from CSR caused by congestive heart failure (CHF) using an implanted medical device, comprising:
   a CSR periodicity determination unit operative to determine a periodicity associated with CSR for the patient; and
   a CSR discrimination unit operative to determine whether the CSR of the patient is caused by CSA or by CHF based on the periodicity associated with CSR for the patient.

19. The implantable cardiac stimulation system of claim 18 and further comprising:
   a CSA/CHF therapy controller operative to control delivery of therapy to the patient based on the determination of whether the CSR of the patient is caused by CSA or by CHF.

20. A system for distinguishing Cheyne-Stokes Respiration (CSR) within a patient caused by central sleep apnea (CSA) from CSR caused by congestive heart failure (CHF) using an implanted medical device, comprising:
   means for detecting the onset of CSR;
   means for detecting a periodicity associated with CSR for the patient; and
   means for determining whether the CSR of the patient is caused by CSA or by CHF based on the periodicity.

* * * * *